(12) United States Patent
Mach et al.

(10) Patent No.: US 9,850,304 B2
(45) Date of Patent: Dec. 26, 2017

(54) ANTI-CD3 ANTIBODIES AND METHODS OF USE THEREOF

(71) Applicant: NovImmune S.A., Geneva (CH)

(72) Inventors: Bernard Mach, Chambesy (CH); Yann Dean, Bossey (FR); Marie Kosco-Vilbois, Minzier (FR); Greg Elson, Collonges sous Saleve (FR); Nicolas Fischer, Geneva (CH); Olivier Leger, St. Sixt (FR)

(73) Assignee: NOVIMMUNE S.A. (CH)

( * ) Notice: Subject to any disclaimer, the term of this patent is extended or adjusted under 35 U.S.C. 154(b) by 807 days.

(21) Appl. No.: 14/048,565

(22) Filed: Oct. 8, 2013

(65) Prior Publication Data

US 2014/0193399 A1 Jul. 10, 2014

Related U.S. Application Data

(63) Continuation of application No. 12/750,385, filed on Mar. 30, 2010, now Pat. No. 8,551,478, which is a continuation of application No. 11/145,131, filed on Jun. 3, 2005, now Pat. No. 7,728,114.

(60) Provisional application No. 60/609,153, filed on Sep. 10, 2004, provisional application No. 60/576,483, filed on Jun. 3, 2004.

(51) Int. Cl.
*A61K 39/395* (2006.01)
*C07K 16/28* (2006.01)
*A61K 45/06* (2006.01)

(52) U.S. Cl.
CPC ...... *C07K 16/2809* (2013.01); *A61K 39/3955* (2013.01); *A61K 45/06* (2013.01); *C07K 2317/21* (2013.01); *C07K 2317/34* (2013.01); *C07K 2317/52* (2013.01); *C07K 2317/56* (2013.01); *C07K 2317/565* (2013.01); *C07K 2317/74* (2013.01)

(58) Field of Classification Search
None
See application file for complete search history.

(56) References Cited

U.S. PATENT DOCUMENTS

| | | | |
|---|---|---|---|
| 5,530,101 A | 6/1996 | Queen et al. |
| 5,545,807 A | 8/1996 | Surani et al. |
| 5,585,089 A | 12/1996 | Queen et al. |
| 5,624,821 A | 4/1997 | Winter et al. |
| 5,648,260 A | 7/1997 | Winter et al. |
| 5,693,761 A | 12/1997 | Queen et al. |
| 5,693,792 A | 12/1997 | Torii et al. |
| 5,714,350 A | 2/1998 | Co et al. |
| 5,777,085 A | 7/1998 | Co et al. |
| 5,834,597 A | 11/1998 | Tso et al. |
| 5,859,205 A | 1/1999 | Adair et al. |
| 5,885,573 A | 3/1999 | Bluestone et al. |
| 6,075,181 A | 6/2000 | Kucherlapati et al. |
| 6,113,901 A | 9/2000 | Bluestone |
| 6,143,297 A | 11/2000 | Bluestone |
| 6,150,584 A | 11/2000 | Kucherlapati et al. |
| 6,406,696 B1 | 6/2002 | Bluestone |
| 6,491,916 B1 | 12/2002 | Bluestone et al. |
| 6,521,404 B1 | 2/2003 | Griffiths et al. |
| 7,041,289 B1 | 5/2006 | Bach et al. |
| 7,728,114 B2 | 6/2010 | Mach et al. |
| 8,551,478 B2 | 10/2013 | Mach et al. |
| 2003/0108548 A1 | 6/2003 | Bluestone et al. |
| 2003/0216551 A1 | 11/2003 | Delovitch |
| 2003/0235583 A1 | 12/2003 | Sturis et al. |
| 2004/0037826 A1 | 2/2004 | Michelsen et al. |
| 2006/0002933 A1 | 1/2006 | Bluestone |
| 2006/0165691 A1 | 7/2006 | Bolt et al. |
| 2006/0165692 A1 | 7/2006 | Bolt et al. |
| 2006/0165693 A1 | 7/2006 | Bolt et al. |
| 2006/0275292 A1 | 12/2006 | Delovitch |
| 2006/0292142 A1 | 12/2006 | Bluestone et al. |
| 2007/0077246 A1 | 4/2007 | Koenig et al. |
| 2007/0178092 A1 | 8/2007 | Bolt et al. |
| 2007/0190045 A1 | 8/2007 | Herold et al. |
| 2007/0190052 A1 | 8/2007 | Herold et al. |

(Continued)

FOREIGN PATENT DOCUMENTS

RU 2179862 C1 2/2002
WO WO 92/01047 1/1992

(Continued)

OTHER PUBLICATIONS

Chatneoud et al., The journal of Immunology, 1997, 158: 2947-2954.*
Lonberg et al., Nature. Apr. 28, 1994;368(6474):856-9.*
Mendez et al., Nat Genet. Feb. 1997;15(2):146-56.*
GenBank Accession Nos. NP000724, published Dec. 23, 2003, "CD3E antigen, epsilon polypeptide (TiT3 complex)," pp. 1-3.*
Harlow et al. (Antibodies, A Laboratory Manual, Cold Spring Harbor laboratory, 1988, pp. 37-47).*
Bradbury et al., Journal of Immunological Methods 290 (2004) 29-49.*

(Continued)

*Primary Examiner* — Zachary Skelding
(74) *Attorney, Agent, or Firm* — Cooley LLP; Ivor Elrifi; Cynthia Kozakiewicz

(57) ABSTRACT

The present invention is related to antibodies directed to the antigen CD3 and uses of such antibodies. In particular, the present invention provides fully human monoclonal antibodies directed to CD3. Nucleotide sequences encoding, and amino acid sequences comprising, heavy and light chain immunoglobulin molecules, particularly sequences corresponding to contiguous heavy and light chain sequences spanning the framework regions and/or complementarity determining regions (CDR's), specifically from FR1 through FR4 or CDR1 through CDR3, are provided. Hybridomas or other cell lines expressing such immunoglobulin molecules and monoclonal antibodies are also provided.

3 Claims, 15 Drawing Sheets

(56) References Cited

U.S. PATENT DOCUMENTS

| | | |
|---|---|---|
| 2007/0224191 A1 | 9/2007 | Walters et al. |
| 2008/0095766 A1 | 4/2008 | Koenig et al. |

FOREIGN PATENT DOCUMENTS

| | | |
|---|---|---|
| WO | WO 94/28027 | 12/1994 |
| WO | WO 97/44362 | 11/1997 |
| WO | WO 03/026692 | 4/2003 |
| WO | WO 2004/052397 | 6/2004 |
| WO | WO 2004/106380 | 12/2004 |
| WO | WO 2005/048935 | 6/2005 |
| WO | WO 2007/117600 | 10/2007 |
| WO | WO 2007/145941 | 12/2007 |
| WO | WO 2007/147090 | 12/2007 |
| WO | WO 2008/079713 | 7/2008 |
| WO | WO 2008/119567 | 10/2008 |

OTHER PUBLICATIONS de Wildt et al., Nat Biotechnol. Sep. 2000;18(9):989-94.*
Adair et al., "Humanization of the murine anti-human CD3 monoclonal antibody OKT3," Hum. Antibod. Hybridomas 5(1-2):41-47 (1994).
Amemiya et al., "Downregulation of TGF-βmRNA and Protein in the Muscles of Patients with Inflammatory Myopathies after Treatment with High-Dose Intravenous Immunoglobulin," Clinical Immunology, 94(2):99-104 (2000).
Bose et al., "Problems in using statistical analysis of replacement and silent mutations in antibody genes for determining antigen-driven affinity selection," Immunology, 116:172-183 (2005).
Chatenoud, "CD3 antibody treatment stimulates the functional capability of regulatory T cells," Novartis Foundation Symposium, 252:279-86 (2003).
Chothia et al., "Canonical structures for the hypervariable regions of immunoglobulins," J. Mol. Biol. 1964(4):901-917 (1987).
Chothia et al., "Conformations of immunoglobulin hypervariable regions," Nature 342:877-883 (1989).
Frank et al., "SPOT synthesis. Epitope analysis with arrays of synthetic peptides prepared on cellulose membranes," Meth. Mol. Biol. Chapter 15, 66:149-169 (1996).
Geysen et al., "Strategies for epitope analysis using peptide synthesis," J. Immunol. Meth., 102(2):259-271 (1987).
Gonzalez et al., "SDR grafting of a murine antibody using multiple human germline templates to minimize its immunogenicity," 41(9):863-72 (2004).
Green et al., "Antigen-specific human monoclonal antibodies from mice engineered with human Ig heavy and light chain YACs," Nat. Gen., 7:13-21 (1994).
Hayward et al., "Lysis of CD3 hybridoma targets by cloned human CD4 lymphocytes," Immunol., 64(1):87-92 (1988).
He et al., "Small-Molecule Inhibition of TNF-α," Science, 310(5750):1022-5 (2005).
International Search Report for PCT/US2005/019922, dated May 3, 2006.
Kim et al., "When does rheumatoid arthritis begin and why do we need to know," Arthritis & Rheumatism, 43(3):473-484 (2000).

Kraan et al., "Asymptomatic synovitis precedes clinically manifest arthritis," Arthritis & Rheumatism, 41(8):1481-8 (1998).
Kramer et al., "Synthesis and screening of peptide libraries on continuous cellulose membrane supports," Meth. Mol. Biol., Chapter 4, 87:25-39 (1998).
Kung et al., "Creating a useful panel of anti-T cell monoclonal antibodies," Int. J. Immunopharmacol., 3 (3): 175-181 (1981).
Kung et al., "Monoclonal antibodies defining distinctive human T cell surface antigens,"Science, 206:347-349 (1979).
Kung et al., "Strategies for generating monocolonal antibodies defining human lymphocyte differentiation antigens," Transplant. Proc., XII(3—Suppl. 1):141-146 (1980).
Ledbetter et al., "Valency of CD3 binding and internalization of the CD3 cell-surface complex control T cell responses to second signals: distinction between effects on protein kinase C, cytoplasmic free calcium, and proliferation," J. Immunol., 136(11):3945-3952 (1986).
Liu et al., "Chimeric mouse-human IgG1 antibody that can mediate lysis of cancer cells," Proc. Natl. Acad. Sci. USA, 84:3439-3443 (1987).
Liu et al., "Production of a mouse-human chimeric monoclonal antibody to CD20 with ptoent Fc-dependent biologic activity," J. Immunol., 139(10):3521-3526 (1987).
Maini et al., "Infliximab (chimeric anti-tumour necrosis factor a monoclonal antibody) versus placeboin rheumatoid arthritis patients receiving concomitant methotrexate: a randomised phase III trial," Lancet, 354(9194):1932-39 (1999).
Malfait et al., "Chronic Relapsing Homologous Collagen-Induced Arthritis in DBA/1 Mice as a Model for Testing Disease-Modifying and Remission-Inducing Therapies," Arthritis & Rheumatism, 44(5):1215-1224 (2001).
Morgan et al., "Synthetic Fc peptide-mediated regulation of the immune response. I. Characterization of the immunomodulatingn properties of a synthetic 23-amino acid peptide derived from the sequence of the CH3 domain of human IgG1," J. Exp. Med., 157(3):947-956 (1983).
Padlan, "Anatomy of the antibody molecule," Mol. Immunol., 31(3):169-217 (1994).
Portolano, S. et al., "Lack of promiscuity in autoantigen-specific H and L chain combinations as revealed by human H and L chain roulette", J. Immunol, 150(3):887-7 (1993).
Renders et al., "Engineered CD3 antibodies for immunosuppression," Clin. Exp. Immunol., 133(3):307-309 (2003).
Uzel et al., "Cytokines in juvenile dermatomyositis pathophysiology: potential and challenge," Current Opinion in Rheumatology, 15(6):691-697 (2003).
Webster's New World Dictionary, Third College Edition, pp. 1067-1068 (1988).
Winter et al., "Humanized antibodies," Immunol. Today, 14(6):243-246 (1993).
Wright et al., "Genetically engineered antibodies: progress and prospects," Crit. Rev. Immunol., 12(3,4):125-168 (1992).
Xu et al., "In vitro characterization of five humanized OKT3 effector function variant antibodies," Cell. Immunol., 200(1):16-26 (2000).
Yang et al., "A common pathway for T lymphocyte activation involving both the CD3Ti complex and CD2 sheep erythrocyte receptor determinants," J. Immunol., 137(4):1097-1100 (1986).

* cited by examiner

Figure 1A

>28F11 VH nucleotide sequence: (SEQ ID NO: 1)

CAGGTGCAGCTGGTGGAGTCCGGGGGAGGCGTGGTCCAGCCTGGGAGGTCCCTGAGACT
CTCCTGTGCAGCGTCTGGATTCAAGTTCAGTGGCTATGGCATGCACTGGGTCCGCCAGG
CTCCAGGCAAGGGGCTGGAGTGGGTGGCAGTTATATGGTATGATGGAAGTAAGAAATAC
TATGTAGACTCCGTGAAGGGCCGCTTCACCATCTCCAGAGACAATTCCAAGAACACGCT
GTATCTGCAAATGAACAGCCTGAGAGCCGAGGACACGGCTGTGTATTACTGTGCGAGAC
AAATGGGCTACTGGCACTTCGATCTCTGGGGCCGTGGCACCCTGGTCACTGTCTCCTCA

Figure 1B

>28F11 VH amino acid sequence: (SEQ ID NO: 2)

QVQLVESGGGVVQPGRSLRLSCAASGFKFS GYGMH WVRQAPGKGLEWVA VIWYDGSKKY
YVDSVKG RFTISRDNSKNTLYLQMNSLRAEDTAVYYCAR QMGYWHFDL WGRGTLVTVSS

Figure 1C

>28F11 VL nucleotide sequence: (SEQ ID NO: 3)

GAAATTGTGTTGACACAGTCTCCAGCCACCCTGTCTTTGTCTCCAGGGGAAAGAGCCAC
CCTCTCCTGCAGGGCCAGTCAGAGTGTTAGCAGCTACTTAGCCTGGTACCAACAGAAAC
CTGGCCAGGCTCCCAGGCTCCTCATCTATGATGCATCCAACAGGGCCACTGGCATCCCA
GCCAGGTTCAGTGGCAGTGGGTCTGGGACAGACTTCACTCTCACCATCAGCAGCCTAGA
GCCTGAAGATTTTGCAGTTTATTACTGTCAGCAGCGTAGCAACTGGCCTCCGCTCACTT
TCGGCGGAGGGACCAAGGTGGAGATCAAA

Figure 1D

>28F11 VL amino acid sequence: (SEQ ID NO: 4)

EIVLTQSPATLSLSPGERATLSC RASQSVSSYLA WYQQKPGQAPRLLIY DASNRAT GIP
ARFSGSGSGTDFTLTISSLEPEDFAVYYC QQRSNWPPLT FGGGTKVEIK

Figure 2A

>23F10 VH nucleotide sequence: (SEQ ID NO: 5)
CAGGTGCAGCTGGTGCAGTCCGGGGGAGGCGTGGTCCAGTCTGGGAGGTCCCTGAGACT
CTCCTGTGCAGCGTCTGGATTCAAGTTCAGTGGCTATGGCATGCACTGGGTCCGCCAGG
CTCCAGGCAAGGGGCTGGAGTGGGTGGCAGTTATATGGTATGATGGAAGTAAGAAATAC
TATGTAGACTCCGTGAAGGGCCGCTTCACCATCTCCAGAGACAATTCCAAGAACACGCT
GTATCTGCAAATGAACAGCCTGAGAGGCGAGGACACGGCTGTGTATTACTGTGCGAGAC
AAATGGGCTACTGGCACTTCGATCTCTGGGGCCGTGGCACCCTGGTCACTGTCTCCTCA

Figure 2B

>23F10 VH amino acid sequence: (SEQ ID NO: 6)
QVQLVQSGGGVVQSGRSLRLSCAASGFKFS GYGMH WVRQAPGKGLEWVAV IWYDGSKKY
YVDSVKG RFTISRDNSKNTLYLQMNSLRGEDTAVYYCAR QMGYWHFDL WGRGTLVTVSS

Figure 2C

>23F10 VL nucleotide sequence: (SEQ ID NO: 7)
GAAATTGTGTTGACACAGTCTCCAGCCACCCTGTCTTTGTCTCCAGGGGAAAGAGCCAC
CCTCTCCTGCAGGGCCAGTCAGAGTGTTAGCAGCTACTTAGCCTGGTACCAACAGAAAC
CTGGCCAGGCTCCCAGGCTCCTCATCTATGATGCATCCAACAGGGCCACTGGCATCCCA
GCCAGGTTCAGTGGCAGTGGGTCTGGGACAGACTTCACTCTCACCATCAGCAGCCTAGA
GCCTGAAGATTTTGCAGTTTATTACTGTCAGCAGCGTAGCAACTGGCCTCCGCTCACTT
TCGGCGGAGGGACCAAGGTGGAGATCAAA

Figure 2D

>23F10 VL amino acid sequence: (SEQ ID NO: 8)
EIVLTQSPATLSLSPGERATLSC RASQSVSSYLA WYQQKPGQAPRLLIY DASNRAT GIP
ARFSGSGSGTDFTLTISSLEPEDFAVYYC QQRSNWPPLT FGGGTKVEIK

Figure 3A

>27H5 VH nucleotide sequence: (SEQ ID NO: 9)

CAGGTGCAGCTGGTGGAGTCCGGGGGAGGCGTGGTCCAGCCTGGGAGGTCCCTGAGACT
CTCCTGTGCAGCGTCTGGATTCACCTTCAGAAGCTATGGCATGCACTGGGTCCGCCAGG
CTCCAGGCAAGGGGCTGGAGTGGGTGGCAATTATATGGTATGATGGAAGTAAAAAAAAC
TATGCAGACTCCGTGAAGGGCCGATTCACCATCTCCAGAGACAATTCCAAGAACACGCT
GTATCTGCAAATGAACAGCCTGAGAGCCGAGGACACGGCTGTGTATTACTGTGCGAGAG
GAACTGGGTACAACTGGTTCGACCCCTGGGGCCAGGGAACCCTGGTCACCGTCTCCTCA

Figure 3B

>27H5 VH amino acid sequence: (SEQ ID NO: 10)

QVQLVESGGGVVQPGRSLRLSCAASGFTFR SYGMH WVRQAPGKGLEWVA IIWYDGSKKN
YADSVKG RFTISRDNSKNTLYLQMNSLRAEDTAVYYCAR GTGYNWFDP WGQGTLVTVSS

Figure 3C

>27H5 VL1 nucleotide sequence: (SEQ ID NO: 11)

GAAATTGTGTTGACACAGTCTCCACGCACCCTGTCTTTGTCTCCAGGGGAAAGAGCCAC
CCTCTCCTGCAGGGCCAGTCAGAGTGTTAGCAGCAGCTACTTAGCCTGGTACCAGCAGA
AACCTGGCCAGGCTCCCAGGCTCCTCATCTATGGTGCATCCAGCAGGGCCACTGGCATC
CCAGACAGGTTCAGTGGCAGTGGGTCTGGGACAGACTTCACTCTCACCATCAGCAGACT
GGACCCTGAAGATTTTGCAGTGTATTACTGTCAGCAGTATGGTAGCTCACCGATCACCT
TCGGCCAAGGGACACGACTGGAGATTAAA

>27H5 VL2 nucleotide sequence: (SEQ ID NO: 12)

GACATCCTGATGACCCAGTCTCCATCCTCCCTGTCTGCATCTGTAGGAGACAGAGTCAC
CATCACTTGCCGGGCAAGTCAGGGCATTAGCAGTGCTTTAGCCTGGTATCAGCAGAAAC
CAGGGAAAGCTCCTAAGCTCCTGATCTATTATGCATCCAGTTTGCAAAGTGGGGTCCCA
TCAAGGTTCAGCGGCAGTGGATCTGGGACGGATTACACTCTCACCATCAGCAGCCTGCA
GCCTGAAGATTTTGCAACTTATTACTGTCAACAGTATTATAGTACCCTCACTTTCGGCG
GAGGGACCAAGGTGGAGATCAAA

Figure 3C Cont'd

>27H5 VL3 nucleotide sequence: (SEQ ID NO: 13)
GACATCGTGATGACCCAGTCTCCATCCTCCCTGTCTGCATCTGTAGGAGACAGAGTCAC
CATCACTTGCCGGGCAAGTCAGGGCATTAGCAGTGCTTTAGCCTGGTATCAGCAGAAAC
CAGGGAAAGCTCCTAAGCTCCTGATCTATGATGCCTCCAGTTTGGGAAGTGGGGTCCCA
TCAAGGTTCAGCGGCAGTGGATCTGGGACAGATTTCACTCTCACCATCAGCAGCCTGCA
GCCTGAAGATTTTGCAACTTATTACTGTCAACAGTATTATAGTACCCTCACTTTCGGCG
GAGGGACCAAGGTGGAGATCAAA >27H5 VL4 nucleotide sequence: (SEQ ID NO: 14)
GACATCCAGATGACCCAGTCTCCATTCTCCCTGTCTGCATCTGTAGGAGACAGAGTCAC
CATCACTTGCTGGGCCAGTCAGGGCATTAGCAGTTATTTAGCCTGGTATCAGCAAAAAC
CAGCAAAAGCCCCTAAGCTCTTCATCTATTATGCATCCAGTTTGCAAAGTGGGGTCCCA
TCAAGGTTCAGCGGCAGTGGATCTGGGACGGATTACACTCTCACCATCAGCAGCCTGCA
GCCTGAAGATTTTGCAACTTATTACTGTCAACAGTATTATAGTACCCTCACTTTCGGCG
GAGGGACCAAGGTGGAGATCAAA >27H5 VL5 nucleotide sequence: (SEQ ID NO: 15)
GACATCGAGATGACCCAGTCTCCATTCTCCCTGTCTGCATCTGTAGGAGACAGAGTCAC
CATCACTTGCTGGGCCAGTCAGGGCATTAGCAGTTATTTAGCCTGGTATCAGCAAAAAC
CAGCAAAAGCCCCTAAGCTCTTCATCTATTATGCATCCAGTTTGCAAAGTGGGGTCCCA
TCAAGGTTCAGCGGCAGTGGATCTGGGACGGATTACACTCTCACCATCAGCAGCCTGCA
GCCTGAAGATTTTGCAACTTATTACTGTCAACAGTATTATAGTACCCTCACTTTCGGCG
GAGGGACCAAGGTGGAGATCAAA

Figure 3D

>27H5 VL1 amino acid sequence: (SEQ ID NO: 16)
EIVLTQSPRTLSLSPGERATLSC RASQSVSSSYLA WYQQKPGQAPRLLIY GASSRAT GI
PDRFSGSGSGTDFTLTISRLDPEDFAVYYC QQYGSSPIT FGQGTRLEIK

Figure 3D Cont'd

>27H5 VL2 amino acid sequence: (SEQ ID NO: 17)
DILMTQSPSSLSASVGDRVTITC<u>RASQGISSALA</u>WYQQKPGKAPKLLIY<u>YASSLQS</u>GVP
SRFSGSGSGTDYTLTISSLQPEDFATYYC<u>QQYYSTLT</u>FGGGTKVEIK >27H5 VL3 amino acid sequence: (SEQ ID NO: 18)
DIVMTQSPSSLSASVGDRVTITC<u>RASQGISSALA</u>WYQQKPGKAPKLLIY<u>DASSLGS</u>GVP
SRFSGSGSGTDFTLTISSLQPEDFATYYC<u>QQYYSTLTF</u>GGGTKVEIK >27H5 VL4 amino acid sequence: (SEQ ID NO: 19)
DIQMTQSPFSLSASVGDRVTITC<u>WASQGISSYLA</u>WYQQKPAKAPKLFIY<u>YASSLQS</u>GVP
SRFSGSGSGTDYTLTISSLQPEDFATYYC<u>QQYYSTLTF</u>GGGTKVEIK >27H5 VL5 amino acid sequence: (SEQ ID NO: 20)
DIEMTQSPFSLSASVGDRVTITC<u>WASQGISSYLA</u>WYQQKPAKAPKLFIY<u>YASSLQS</u>GVP
SRFSGSGSGTDYTLTISSLQPEDFATYYC<u>QQYYSTLTF</u>GGGTKVEIK

Figure 3E

```
27H5 VL4   DIQMTQSPFSLSASVGDRVTITCWASQGISS-YLAWYQQKPAKAPKLFIYYASSLQSGVP  59
27H5 VL5   DIEMTQSPFSLSASVGDRVTITCWASQGISS-YLAWYQQKPAKAPKLFIYYASSLQSGVP  59
27H5 VL2   DILMTQSPSSLSASVGDRVTITCRASQGISS-ALAWYQQKPGKAPKLLIYYASSLQSGVP  59
27H5 VL3   DIVMTQSPSSLSASVGDRVTITCRASQGISS-ALAWYQQKPGKAPKLLIYDASSLGSGVP  59
27H5 VL1   EIVLTQSPPTLSLSPGERATLSCRASQSVSSSYLAWYQQKPGQAPRLLIYGASSRATGIP  60
    KEY    :* ;**** :** *:* *;;: ***;:**  ******.;**:*;** ***   :*;:*

27H5 VL4   SRFSGSGSGTDYTLTISSLQPEDFATYYCQQYYST-LTFGGGTKVEIK 106   (SEQ ID NO: 19)
27H5 VL5   SRFSGSGSGTDYTLTISSLQPEDFATYYCQQYYST-LTFGGGTKVEIK 106   (SEQ ID NO: 20)
27H5 VL2   SRFSGSGSGTDYTLTISSLQPEDFATYYCQQYYST-LTFGGGTKVEIK 106   (SEQ ID NO: 17)
27H5 VL3   SRFSGSGSGTDFTLTISSLQPEDFATYYCQQYYST-LTFGGGTKVEIK 106   (SEQ ID NO: 18)
27H5 VL1   DRFSGSGSGTDFTLTISRLDPEDFAVYYCQQYGSSPITFGQGTRLEIK 108   (SEQ ID NO:16)
    KEY    .******.**;***** * *;**** .****  *;  :*** **;;***
```

Figure 4A

>15C3 VH nucleotide sequence: (SEQ ID NO: 21)
CAGGTGCAGCTGGTGCAGTCTGGGGGAGGCGTGGTCCAGCCCGGGAGGTCCCTGAGACT
CTCCTGTGTAGCGTCTGGATTCACCTTCAGTAGCTATGGCATGCACTGGGTCCGCCAGG
CTCCAGGCAAGGGGCTGGAGTGGGTGGCAGCTATATGGTATAATGGAAGAAAACAAGAC
TATGCAGACTCCGTGAAGGGCCGATTCACCATCTCCAGAGACAATTCCAAGAACACGCT
GTATCTGCAAATGAACAGCCTGAGAGCCGAGGACACGGCTGTGTATTACTGTACGAGGG
GAACTGGGTACAATTGGTTCGACCCCTGGGGCCAGGGAACCCTGGTCACCGTCTCCTCA

Figure 4B

>15C3 VH amino acid sequence: (SEQ ID NO: 22)
QVQLVQSGGGVVQPGRSLRLSCVASGFTFS SYGMH WVRQAPGKGLEWVA AIWYNGRKQD
YADSVKG RFTISRDNSKNTLYLQMNSLRAEDTAVYYCTR GTGYNWFDP WGQGTLVTVSS

Figure 4C

>15C3 VL1 nucleotide sequence: (SEQ ID NO: 23)
GAAATTGTGTTGACACAGTCTCCAGCCACCCTGTCTTTGTCTCCAGGGGAAAGAGCCAC
CCTCTCCTGCAGGGCCAGTCAGAGTGTTAGCAGCTACTTAGCCTGGTACCAACAGAAAC
CTGGCCAGGCTCCCAGGCTCCTCATCTATGATGCATCCAACAGGGCCACTGGCATCCCA
GCCAGGTTCAGTGGCAGTGGGTCTGGGACAGACTTCACTCTCACCATCAGCAGCCTAGA
GCCTGAAGATTTTGCAGTTTATTACTGTCAGCAGCGTAGCAACTGGCCGTGGACGTTCG
GCCAAGGGACCAAGGTGGAAATCAAA >15C3 VL2 nucleotide sequence: (SEQ ID NO: 24)
GCCATCCAGTTGACCCAGTCTCCATCCTCCCTGTCTGCATCTGTATGAGACAGAGTCAC
CATCACTTGCCGGGCAAGTCAGGGCATTAGCAGTGCTTTAGCCTGGTATCAGCAGAAAC
CAGGGAAAGCTCCTAAGCTCCTGATCTATGATGCCTCCAGTTTGGAAAGTGGGGTCCCA
TCAAGGTTCAGCGGCAGTGGATCTGGGACAGATTTCACTCTCACCATCAGCAGCCTGCA
GCCTGAAGATTTTGCAACTTATTACTGTCAACAGTTTAATAGTTACCCTATCACCTTCG
GCCAAGGGACACGACTGGAGATTAAA

Figure 4D

>15C3 VL1 amino acid sequence: (SEQ ID NO: 25)
EIVLTQSPATLSLSPGERATLSCRASQSVSSYLAWYQQKPGQAPRLLIYDASNRATGIP
ARFSGSGSGTDFTLTISSLEPEDFAVYYCQQRSNWPWTFGQGTKVEIK >15C3 VL2 amino acid sequence: (SEQ ID NO: 26)
AIQLTQSPSSLSASVGDRVTITCRASQGISSALAWYQQKPGKAPKLLIYDASSLESGVP
SRFSGSGSGTDFTLTISSLQPEDFATYYCQQFNSYPITFGQGTRLEIK

Figure 5

V_H sequence alignments of CD3 binders
VH3

```
                        CDR1                                    CDR2
                        ----                                    ----
15C3    QVQLVQSGGGVVQPGRSLRLSCVASGFTFS SYGMH WVRQAPGKGLEWVA A IWYNGRKQDY
27H5    QVQLVESGGGVVQPGRSLRLSCAASGFTFR SYGMH WVRQAPGKGLEWVA I IWYDGSKKNY
28F11   QVQLVESGGGVVQPGRSLRLSCAASGFKFS GYGMH WVRQAPGKGLEWVA V IWYDGSKKYY
DP-50   QVQLVESGGGVVQPGRSLRLSCAASGFTFS SYGMH WVRQAPGKGLEWVA V IWYDGSNKYY
        *****:************** ***:***:  .****  ***************  .*:*:. *

CDR2
                ----
15C3    ADSVKG RFTISRDNSKNTLYLQMNSLRAEDTAVYYCCTR GTGY NWFDPWGQGTLVTVSS    (SEQ ID NO:22)
27H5    ADSVKG RFTISRDNSKNTLYLQMNSLRAEDTAVYYCAR  GTGY NWFDPWGQGTLVTVSS    (SEQ ID NO:10)
                                                D    J
28F11   VDSVKG RFTISRDNSKNTLYLQMNSLRAEDTAVYYCAR QMGYWHFDLWGRGTLVTVSS     (SEQ ID NO:2)
DP-50   ADSVKG RFTISRDNSKNTLYLQMNSLRAEDTAVYYCAR                          (SEQ ID NO:48)
        .*****.*********************************.         *

Human heavy joining 5-02                NWFDPWGQGTLVTVSS                (SEQ ID NO:49)
Human heavy joining 2                   YWYFDLWGRGTLVTVSS               (SEQ ID NO:50)
```

Figure 6

V_L sequence alignments of CD3 binders

VκIII

```
                  CDR1                                            CDR2
                  ---------                                        --------
28F11     EIVLTQSPATLSLSPGERATLSC RASQSVSSYLA WYQQKPGQAPRLLIY DASNRAT GIPA
15C3 VL1  EIVLTQSPATLSLSPGERATLSC RASQSVSSYLA WYQQKPGQAPRLLIY DASNRAT GIPA
L6        EIVLTQSPATLSLSPGERATLSC RASQSVSSYLA WYQQKPGQAPRLLIY DASNRAT GIPA
          ****************************************************** *******
```

```
                                              CDR3                        J
                                              ---------                   ------
28F11     RFSGSGSGTDFTLTISSLEPEDFAVYYC QQRSNWPPLT FGGGTKVEIK    (SEQ ID NO:4)
15C3 VL1  RFSGSGSGTDFTLTISSLEPEDFAVYYC QQRSNWP.WT FGQGTKVEIK    (SEQ ID NO:25)
L6        RFSGSGSGTDFTLTISSLEPEDFAVYYC QQRSNWP   ----------     (SEQ ID NO:70)
          ***************************************

Human Kappa Joining 4                                    LTFGGGTKVEIK  (SEQ ID NO:51)
Human Kappa Joining 1                                    WTFGQGTKVEIK  (SEQ ID NO:52)
```

Figure 7

V_L sequence alignments of CD3 binders

VkI

```
                                CDR1                                            CDR2
                                -----                                           ----
27H5(19)    DILMTQSPSSLSASVGDRVTITCRASQGISSALAWYQQKPGKAPKLLIYASSLQSGVPS
15C3 VL2    AIQLTQSPSSLSASVGDRVTITCRASQGISSALAWYQQKPGKAPKLLIYDASSLESGVPS
L4/18a      AIQLTQSPSSLSASVGDRVTITCRASQGISSALAWYQQKPGKAPKLLIYDASSLESGVPS
            .*:*************************************************:****

CDR3                        J
                                            ----                        -
27H5(19)    RFSGSGSGTDYTLTISSLQPEDFATYYCQQYYST.LITFGGGTKVEIK          (SEQ ID NO:17)
15C3 VL2    RFSGSGSGTDFTLTISSLQPEDFATYYCQQFNSYPIIFGQGTRLEIK          (SEQ ID NO:26)
L4/18a      RFSGSGSGTDFTLTISSLQPEDFATYYCQQFNSYP------                (SEQ ID NO:53)
            **********:****************:**.  :

Human Kappa Joining 4           LTFGGGTKVEIK                             (SEQ ID NO:54)
Human Kappa Joining 5           ITFGQGTRLEIK                             (SEQ ID NO:55)
```

Figure 8

V_L sequence alignments of CD3 binders

VkII

```
                      CDR1                              CDR2
                      ----                              ----
27H5(13.17)  EIVLTQSPRTLSLSPGERATLSC RASQSVSSSYLA WYQQKPGQAPRLLIY GASSRAT GIP
DPK22        EIVLTQSPGTLSLSPGERATLSC RASQSVSSSYLA WYQQKPGQAPRLLIY GASSRAT GIP
             ********.************************************************

CDR3
                                              ----
                                                              J
                                                              -
27H5         DRFSGSGSGTDFTLTISRLDPEDFAVYYC QQYGSSPI FGQGTRLEIK  (SEQ ID NO:16)
DPK22        DRFSGSGSGTDFTLTISRLEPEDFAVYYC QQYGSSP------------  (SEQ ID NO:56)
             ********************.********.*******

Human Kappa Joining 5                                 IFGQGTRLEIK  (SEQ ID NO:57)
```

*Peptide Array: overlapping peptides spanning the extracellular domain of human CD3ε*

TNF-α Release Assay

IFN-γ Release Assay

ANTI-CD3 ANTIBODIES AND METHODS OF USE THEREOF

RELATED APPLICATIONS

This application is a continuation of U.S. patent application Ser. No. 12/750,385, filed Mar. 30, 2010, now issued as U.S. Pat. No. 8,551,478, which is a continuation of U.S. patent application Ser. No. 11/145,131, filed Jun. 3, 2005, now issued as U.S. Pat. No. 7,728,114, which claims the benefit of U.S. Provisional Application No. 60/576,483, filed Jun. 3, 2004 and U.S. Provisional Application No. 60/609,153, filed Sep. 10, 2004, each of which is incorporated herein by reference in its entirety.

INCORPORATION OF SEQUENCE LISTING

The contents of the text file named "407C02USSubSeqList.txt", which was created on Mar. 4, 2014 and is 32.0 KB in size, are hereby incorporated by reference in their entirety.

FIELD OF THE INVENTION

This invention relates generally to fully human anti-CD3 antibodies as well as to methods for use thereof.

BACKGROUND OF THE INVENTION

The body's immune system serves as a defense against a variety of conditions, including, e.g., injury, infection and neoplasia, and is mediated by two separate but interrelated systems, the cellular and humoral immune systems. Generally speaking, the humoral system is mediated by soluble products, termed antibodies or immunoglobulins, which have the ability to combine with and neutralize products recognized by the system as being foreign to the body. In contrast, the cellular immune system involves the mobilization of certain cells, termed T-cells that serve a variety of therapeutic roles.

The immune system of both humans and animals include two principal classes of lymphocytes: the thymus derived cells (T cells), and the bone marrow derived cells (B cells). Mature T cells emerge from the thymus and circulate between the tissues, lymphatics, and the bloodstream. T cells exhibit immunological specificity and are directly involved in cell-mediated immune responses (such as graft rejection). T cells act against or in response to a variety of foreign structures (antigens). In many instances these foreign antigens are expressed on host cells as a result of infection. However, foreign antigens can also come from the host having been altered by neoplasia or infection. Although T cells do not themselves secrete antibodies, they are usually required for antibody secretion by the second class of lymphocytes, B cells.

There are various subsets of T cells, which are generally defined by antigenic determinants found on their cell surfaces, as well as functional activity and foreign antigen recognition. Some subsets of T cells, such as $CD8^+$ cells, are killer/suppressor cells that play a regulating function in the immune system, while others, such as $CD4^+$ cells, serve to promote inflammatory and humoral responses.

Human peripheral T lymphocytes can be stimulated to undergo mitosis by a variety of agents including foreign antigens, monoclonal antibodies and lectins such as phytohemayglutinin and concanavalin A. Although activation presumably occurs by binding of the mitogens to specific sites on cell membranes, the nature of these receptors, and their mechanism of activation, is not completely elucidated. Induction of proliferation is only one indication of T cell activation. Other indications of activation, defined as alterations in the basal or resting state of the cell, include increased lymphokine production and cytotoxic cell activity.

T cell activation is a complex phenomenon that depends on the participation of a variety of cell surface molecules expressed on the responding T cell population. For example, the antigen-specific T cell receptor (TcR) is composed of a disulfide-linked heterodimer, containing two clonally distributed, integral membrane glycoprotein chains, alpha and beta ($\alpha$ and $\beta$), or gamma and delta ($\gamma$ and $\delta$), non-covalently associated with a complex of low molecular weight invariant proteins, commonly designated as CD3 (once referred to as T3).

The TcR alpha and beta chains determine antigen specificities. The CD3 structures represent accessory molecules that are the transducing elements of activation signals initiated upon binding of the TcR alpha beta (TcR $\alpha\beta$) to its ligand. There are both constant regions of the glycoprotein chains of TcR, and variable regions (polymorphisms). Polymorphic TcR variable regions define subsets of T cells, with distinct specificities. Unlike antibodies that recognize whole or smaller fragments of foreign proteins as antigens, the TcR complex interacts with only small peptides of the antigen, which must be presented in the context of major histocompatibility complex (MHC) molecules. These MHC proteins represent another highly polymorphic set of molecules randomly dispersed throughout the species. Thus, activation usually requires the tripartite interaction of the TcR and foreign peptidic antigen bound to the major MHC proteins.

SUMMARY OF THE INVENTION

The present invention provides fully human monoclonal antibodies specifically directed against CD3. Exemplary monoclonal antibodies include 28F11, 27H5, 23F10 and 15C3 described herein. Alternatively, the monoclonal antibody is an antibody that binds to the same epitope as 28F11, 27H5, 23F10 or 15C3. The antibodies are respectively referred to herein is huCD3 antibodies. The huCD3 antibody has one or more of the following characteristics: the antibody binds to CD3 positive (CD3+) cells but not CD3 negative (CD3−) cells; the huCD3 antibody induces antigenic modulation which involves alteration (e.g., decrease) of the cell surface expression level or activity of CD3 or the T cell receptor (TcR); the huCD3 antibody inhibits binding of the murine anti-human OKT3 monoclonal antibody to T-lymphocytes; or the huCD3 antibody binds an epitope of CD3 that wholly or partially includes the amino acid sequence EMGGITQTPYKVSISGT (SEQ ID NO:67). The huCD3 antibodies of the invention compete with the murine anti-CD3 antibody OKT3 for binding to CD3, and exposure to the huCD3 antibody removes or masks CD3 and/or TcR without affecting cell surface expression of CD2, CD4 or CD8. The masking of CD3 and/or TcR results in the loss or reduction of T-cell activation, which is desirable in autoimmune diseases where uncontrolled T-cell activation occurs. Down-regulation of CD3 results in a prolonged effect of reduced T cell activation, e.g., for a period of at least several months, as compared with the transient suppression that is observed when using a traditional immunosuppressive agent, e.g., cyclosporin.

Antigenic modulation refers to the redistribution and elimination of the CD3-T cell receptor complex on the surface of a cell, e.g., a lymphocyte. Decrease in the level of cell surface expression or activity of the TcR on the cell is meant that the amount or function of the TcR is reduced. Modulation of the level of cell surface expression or activity of CD3 is meant that the amount of CD3 on the cell surface or function of CD3 is altered, e.g., reduced. The amount of CD3 or the TcR expressed at the plasma membrane of the cell is reduced, for example, by internalization of CD3 or the TcR upon contact of the cell with the huCD3 antibody. Alternatively, upon contact of a cell with the huCD3 antibody, CD3 or the TcR is masked.

Inhibiting the binding of the murine anti-human OKT3 monoclonal antibody to a T-lymphocyte is defined as a decrease in the ability of the murine OKT3 antibody to form a complex with CD3 on the cell surface of a T-lymphocyte.

A huCD3 antibody contains a heavy chain variable having the amino acid sequence of SEQ ID NOS: 2, 6, 10 or 22 and a light chain variable having the amino acid sequence of SEQ ID NOS: 4, 8, 16-20 or 25-26. Preferably, the three heavy chain CDRs include an amino acid sequence at least 90%, 92%, 95%, 97% 98%, 99% or more identical a sequence selected from the group consisting of GYGMH (SEQ ID NO:27); VIWYDGSKKYYVDSVKG (SEQ ID NO:28); QMGYWHFDL (SEQ ID NO:29); SYGMH (SEQ ID NO:33); IIWYDGSKKNYADSVKG (SEQ ID NO:34); GTGYNWFDP (SEQ ID NO:35); and AIWYNGRKQDY-ADSVKG (SEQ ID NO:44) and a light chain with three CDR that include an amino acid sequence at least 90%, 92%, 95%, 97% 98%, 99% or more identical to a sequence selected from the group consisting of the amino acid sequence of RASQSVSSYLA (SEQ ID NO:30); DASNRAT (SEQ ID NO:31); QQRSNWPPLT (SEQ ID NO:32); RASQSVSSSYLA (SEQ ID NO:36); GASSRAT (SEQ ID NO:37); QQYGSSPIT (SEQ ID NO:38); RASQGISSALA (SEQ ID NO:39); YASSLQS (SEQ ID NO:40); QQYYSTLT (SEQ ID NO:41); DASSLGS (SEQ ID NO:42); WASQGISSYLA (SEQ ID NO:43); QQRSN-WPWT (SEQ ID NO:45); DASSLES (SEQ ID NO:46); and QQFNSYPIT (SEQ ID NO:47). The antibody binds CD3.

A huCD3 antibody of the invention exhibits at least two or more (i.e., two or more, three or more, four or more, five or more, six or more, seven or more, eight or more, nine or more, ten or more, eleven or more) of the following characteristics: the antibody contains a variable heavy chain region ($V_H$) encoded by a human DP50 $V_H$ germline gene sequence, or a nucleic acid sequence that is homologous to the human DP50 $V_H$ germline gene sequence; the antibody contains a variable light chain region ($V_L$) encoded by a human L6 $V_L$ germline gene sequence, or a nucleic acid sequence homologous to the human L6 $V_L$ germline gene sequence; the antibody contains a $V_L$ encoded by a human L4/18a $V_L$ germline gene sequence, or a nucleic acid sequence homologous to the human L4/18a $V_L$ germline gene sequence; the antibody includes a $V_H$ CDR1 region comprising the amino acid sequence YGMH (SEQ ID NO:58); the antibody includes a $V_H$ CDR2 region comprising the amino acid sequence DSVKG (SEQ ID NO:59); the antibody includes a $V_H$ CDR2 region comprises the amino acid sequence IWYX$_1$GX$_2$X$_3$X$_4$X$_5$Y X$_6$DSVKG (SEQ ID NO:60); the antibody includes a $V_H$ CDR3 region comprising the amino acid sequence X$_A$X$_B$GYX$_C$X$_D$FDX$_E$ (SEQ ID NO:61); the antibody includes a $V_H$ CDR3 region comprising the amino acid sequence GTGYNWFDP (SEQ ID NO:62) or the amino acid sequence QMGYWHFDL (SEQ ID NO:63); the antibody includes the amino acid sequence VTVSS (SEQ ID NO:64) at a position that is C-terminal to the CDR3 region, wherein the position is in a variable region C-terminal to the CDR3 region; the antibody includes the amino acid sequence GTLVTVSS (SEQ ID NO:65) at a position that is C-terminal to CDR3 region, wherein the position is in a variable region C-terminal to the CDR3 region; the antibody includes the amino acid sequence WGRGTLVTVSS (SEQ ID NO:66) at a position that is C-terminal to CDR3 region, wherein the position is in a variable region C-terminal to the CDR3 region; the antibody binds an epitope that wholly or partially includes the amino acid sequence EMGGITQTPYKVSISGT (SEQ ID NO:67); and the antibody includes a mutation in the heavy chain at an amino acid residue at position 234, 235, 265, or 297 or combinations thereof, and wherein the release of cytokines from a T-cell in the presence of said antibody is reduced as compared to the release of cytokines from a T-cell in the presence of an antibody that does not include a mutation in the heavy chain at position 234, 235, 265 or 297 or combinations thereof. The numbering of the heavy chain residues described herein is that of the EU index (see Kabat et al., "Proteins of Immunological Interest", US Dept. of Health & Human Services (1983)), as shown, e.g., in U.S. Pat. Nos. 5,624,821 and 5,648,260, the contents of which are hereby incorporated in its entirety by reference.

In some aspects, the huCD3 antibody contains an amino acid mutation. The mutation is in the constant region. The mutation results in an antibody that has an altered effector function. An effector function of an antibody is altered by altering, i.e., enhancing or reducing, the affinity of the antibody for an effector molecule such as an Fc receptor or a complement component. By altering an effector function of an antibody, it is possible to control various aspects of the immune response, e.g., enhancing or suppressing various reactions of the immune system. For example, the mutation results in an antibody that is capable of reducing cytokine release from a T-cell. For example, the mutation is in the heavy chain at amino acid residue 234, 235, 265, or 297 or combinations thereof. Preferably, the mutation results in an alanine residue at either position 234, 235, 265 or 297, or a glutamate residue at position 235, or a combination thereof. The term "cytokine" refers to all human cytokines known within the art that bind extracellular receptors expressed on the cell surface and thereby modulate cell function, including but not limited to IL-2, IFN-gamma, TNF-a, IL-4, IL-5, IL-6, IL-9, IL-10, and IL-13.

The release of cytokines can lead to a toxic condition known as cytokine release syndrome (CRS), a common clinical complication that occurs, e.g., with the use of an anti-T cell antibody such as ATG (anti-thymocyte globulin) and OKT3 (a murine anti-human CD3 antibody). This syndrome is characterized by the excessive release of cytokines such as TNF, IFN-gamma and IL-2 into the circulation. The CRS occurs as a result of the simultaneous binding of the antibodies to CD3 (via the variable region of the antibody) and the Fc Receptors and/or complement receptors (via the constant region of the antibody) on other cells, thereby activating the T cells to release cytokines that produce a systemic inflammatory response characterized by hypotension, pyrexia and rigors. Symptoms of the CRS include fever, chills, nausea, vomiting, hypotension, and dyspnea. Thus, the huCD3 antibody of the invention contains one or more mutations that prevent heavy chain constant region-mediated release of one or more cytokine(s) in vivo.

The fully human CD3 antibodies of the invention include, for example, a $L^{234}\ L^{235} \rightarrow A^{234}\ E^{235}$ mutation in the Fc region, such that cytokine release upon exposure to the huCD3 antibody is significantly reduced or eliminated (see e.g., FIGS. 11A, 11B). As described below in Example 4, the $L^{234}$ $L^{235} \to A^{234}$ $E^{235}$ mutation in the Fc region of the huCD3 antibodies of the invention reduces or eliminates cytokine release when the huCD3 antibodies are exposed to human leukocytes, whereas the mutations described below maintain significant cytokine release capacity. For example, a significant reduction in cytokine release is defined by comparing the release of cytokines upon exposure to the huCD3 antibody having a $L^{234}$ $L^{235} \to A^{234}$ $E^{235}$ mutation in the Fc region to level of cytokine release upon exposure to another anti-CD3 antibody having one or more of the mutations described below. Other mutations in the Fc region include, for example, $L^{234}$ $L^{235} \to A^{234}$ $A^{235}$, $L^{235} \to E^{235}$, $N^{297} \to A^{297}$, and $D^{265} \to A^{265}$.

Alternatively, the huCD3 antibody is encoded by a nucleic acid that includes one or more mutations that replace a nucleic acid residue with a germline nucleic acid residue. By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide. Thus, the antibodies of the invention include one or more mutations that replace a nucleic acid with the germline nucleic acid residue. Germline antibody genes include, for example, DP50 (Accession number: IMGT/EMBL/GenBank/DDBJ:L06618), L6 (Accession number: IMGT/EMBL/GenBank/DDBJ:X01668) and L4/18a (Accession number: EMBL/GenBank/DDBJ: Z00006).

The heavy chain of a huCD3 antibody is derived from a germ line V (variable) gene such as, for example, the DP50 germline gene. The nucleic acid and amino acid sequences for the DP50 germline gene include, for example, the nucleic acid and amino acid sequences shown below:

```
                                          (SEQ ID NO: 68)
tgattcatgg agaaatagag agactgagtg tgagtgaaca tgagtgagaa aaactggatt tgtgtggcat tttctgataa cggtgtcctt ctgtttgcag gtgtccagtg tcaggtgcag ctggtggagt ctgggggagg cgtggtccag cctgggaggt ccctgagact ctcctgtgca gcgtctggat tcaccttcag tagctatggc atgcactggg tccgccaggc tccaggcaag gggctggagt gggtggcagt tatatggtat gatggaagta ataaatacta tgcagactcc gtgaagggcc gattcaccat ctccagagac aattccaaga acacgctgta tctgcaaatg aacagcctga gagccgagga cacggctgtg tattactgtg cgagagacac ag
                                          (SEQ ID NO: 69)
VQCQVQLVES GGGVVQPGRS LRLSCAASGF TFSSYGMHWV

RQAPGKGLEW VAVIWYDGSN KYYADSVKGR FTISRDNSKN

TLYLQMNSLR AEDTAVYYCA R
```

The huCD3 antibodies of the invention include a variable heavy chain ($V_H$) region encoded by a human DP50 $V_H$ germline gene sequence. A DP50 $V_H$ germline gene sequence is shown, e.g., in SEQ ID NO:48 in FIG. 5. The huCD3 antibodies of the invention include a $V_H$ region that is encoded by a nucleic acid sequence that is at least 80% homologous to the DP50 $V_H$ germline gene sequence. Preferably, the nucleic acid sequence is at least 90%, 95%, 96%, 97% homologous to the DP50 $V_H$ germline gene sequence, and more preferably, at least 98%, 99% homologous to the DP50 $V_H$ germline gene sequence. The $V_H$ region of the huCD3 antibody is at least 80% homologous to the amino acid sequence of the $V_H$ region encoded by the DP50 $V_H$ germline gene sequence. Preferably, the amino acid sequence of $V_H$ region of the huCD3 antibody is at least 90%, 95%, 96%, 97% homologous to the amino acid sequence encoded by the DP50 $V_H$ germline gene sequence, and more preferably, at least 98%, 99% homologous to the sequence encoded by the DP50 $V_H$ germline gene sequence.

The huCD3 antibodies of the invention also include a variable light chain ($V_L$) region encoded by a human L6 or L4/18a $V_L$ germline gene sequence. A human L6 $V_L$ germline gene sequence is shown, e.g., in SEQ ID NO:70 in FIG. 6, and a human L4/18a $V_L$ germline gene sequence is shown, for example, in SEQ ID NO:53 in FIG. 7. Alternatively, the huCD3 antibodies include a $V_L$ region that is encoded by a nucleic acid sequence that is at least 80% homologous to either the L6 or L4/18a $V_L$ germline gene sequence. Preferably, the nucleic acid sequence is at least 90%, 95%, 96%, 97% homologous to either the L6 or L4/18a $V_L$ germline gene sequence, and more preferably, at least 98%, 99% homologous to either the L6 or L4/18a $V_L$ germline gene sequence. The $V_L$ region of the huCD3 antibody is at least 80% homologous to the amino acid sequence of the $V_L$ region encoded by either the L6 or L4/18a $V_L$ germline gene sequence. Preferably, the amino acid sequence of $V_L$ region of the huCD3 antibody is at least 90%, 95%, 96%, 97% homologous to the amino acid sequence encoded by either the L6 or L4/18a $V_L$ germline gene sequence, and more preferably, at least 98%, 99% homologous to the sequence encoded by either the L6 or L4/18a $V_L$ germline gene sequence.

The huCD3 antibodies of the invention have, for example, partially conserved amino acid sequences that are derived from the DP50 germline. For example, the CDR1 region of huCD3 antibodies of the invention have at least the contiguous amino acid sequence YGMH (SEQ ID NO: 58).

The CDR2 of the huCD3 antibodies includes, e.g., at least the contiguous amino acid sequence DSVKG (SEQ ID NO:59). For example, the CDR2 region includes the contiguous amino acid sequence IWYX$_1$GX$_2$X$_3$X$_4$X$_5$YX$_6$DSVKG (SEQ ID NO:60), where X$_1$, X$_2$, X$_3$, X$_4$, X$_5$ and X$_6$ represent any amino acid. For example, X$_1$, X$_2$, X$_3$ and X$_4$ are hydrophilic amino acids. In some huCD3 antibodies of the invention, X$_1$ is asparagine or aspartate, X$_2$ is arginine or serine, X$_3$ is lysine or asparagine, X$_4$ is lysine or glutamine, X$_5$ is aspartate, asparagine or tyrosine, and/or X$_6$ is valine or alanine. For example, the $V_H$ CDR2 region includes an amino acid sequence selected from the group consisting of AIWYNGRKQDYADSVKG (SEQ ID NO:44), IIWYDGSKKNYADSVKG (SEQ ID NO:34), VIWYDGSKKYYVDSVKG (SEQ ID NO:28) and VIWYDGSNKYYADSVKG (SEQ ID NO:72).

The CDR3 region of huCD3 antibodies contain, for example, at least the contiguous amino acid sequence X$_A$X$_B$GYX$_C$X$_D$FDX$_E$ (SEQ ID NO:61), where X$_A$, X$_B$, X$_C$, X$_D$, and X$_E$ represent any amino acid. In some huCD3 antibodies of the invention, $X_A$ and $X_B$ are neutral amino acids, $X_D$ is an aromatic amino acid, and/or wherein $X_E$ is a hydrophobic amino acid. For example, $X_A$ is glycine or glutamine, $X_B$ is threonine or methionine, $X_C$ is asparagine or tryptophan, $X_D$ is tryptophan or histidine, and/or $X_E$ is proline or leucine. For example, the CDR3 region includes either the contiguous amino acid sequence GTGYNWFDP (SEQ ID NO:62) or the contiguous amino acid sequence QMGYWHFDL (SEQ ID NO: 63).

The huCD3 antibodies include a framework 2 region (FRW2) that contains the amino acid sequence WVRQAPG-KGLEWV (SEQ ID NO:73). huCD3 antibodies of the invention include a framework 3 region (FRW3) that contains the amino acid sequence RFTISRDNSKNT-LYLQMNSLRAEDTAVYYCA (SEQ ID NO:74).

Some huCD3 antibodies include the contiguous amino acid sequence VTVSS (SEQ ID NO:64) at a position that is C-terminal to CDR3 region. For example, the antibody contains the contiguous amino acid sequence GTLVTVSS (SEQ ID NO:65) at a position that is C-terminal to the CDR3 region. Other huCD3 antibodies include the contiguous amino acid sequence WGRGTLVTVSS (SEQ ID NO: 66) at a position that is C-terminal to the CDR3 region. The arginine residue in SEQ ID NO:66 is shown, for example, in the $V_H$ sequences for the 28F11 huCD3 antibody (SEQ ID NO:2) and the 23F10 huCD3 antibody (SEQ ID NO:6).

In another aspect, the invention provides methods of treating, preventing or alleviating a symptom of an immune-related disorder by administering an huCD3 antibody to a subject. Optionally, the subject is further administered with a second agent such as, but not limited to, anti-inflammatory compounds or immunosuppressive compounds. For example, subjects with Type I diabetes or Latent Autoimmune Diabetes in the Adult (LADA), are also administered a second agent, such as, for example, GLP-1 or a beta cell resting compound (i.e., a compound that reduces or otherwise inhibits insulin release, such as potassium channel openers).

Suitable compounds include, but are not limited to methotrexate, cyclosporin A (including, for example, cyclosporin microemulsion), tacrolimus, corticosteroids, statins, interferon beta, Remicade (Infliximab), Enbrel (Etanercept) and Humira (Adalimumab).

The subject is suffering from or is predisposed to developing an immune related disorder, such as, for example, an autoimmune disease or an inflammatory disorder.

In another aspect, the invention provides methods of administering the huCD3 antibody of the invention to a subject prior to, during and/or after organ or tissue transplantation. For example, the huCD3 antibody of the invention is used to treat or prevent rejection after organ or tissue transplantation.

BRIEF DESCRIPTION OF THE DRAWINGS

FIGS. 1A, 1B, 1C, and 1D are a series of representations of the nucleotide sequence and amino acid sequences for the variable light and variable heavy regions of the huCD3 antibody 28F11. FIG. 1A depicts the nucleotide sequence encoding the variable region of the heavy chain, and FIG. 1B represents the amino acid sequence encoded by the nucleotide sequence shown in FIG. 1A, wherein the CDRs are highlighted with boxes. FIG. 1C depicts the nucleotide sequence encoding the variable region of the light chain, and FIG. 1D represents the amino acid sequence encoded by the nucleotide sequence shown in FIG. 1C, wherein the CDRs are indicated by boxes.

FIGS. 2A, 2B, 2C, and 2D are a series of representations of the nucleotide sequence and amino acid sequences for the variable light and variable heavy regions of the huCD3 antibody 23F10, with FIG. 2A representing the nucleotide sequence encoding the variable region of the heavy chain, FIG. 2B representing the amino acid sequence encoded by the nucleotide sequence shown in FIG. 2A, FIG. 2C representing the nucleotide sequence encoding the variable region of the light chain, and FIG. 2D representing the amino acid sequence encoded by the nucleotide sequence shown in FIG. 2C.

FIGS. 3A, 3B, 3C, 3D, and 3E are a series of representations of the nucleotide sequence and amino acid sequences for the variable light and variable heavy regions of the huCD3 antibody 27H5. FIG. 3A represents the nucleotide sequence encoding the variable region of the heavy chain; FIG. 3B represents the amino acid sequence encoded by the nucleotide sequence shown in FIG. 3A; FIG. 3C represents the five nucleotide sequences encoding the variable region of the light chain for the 27H5 clone; FIG. 3D represents the five amino acid sequences encoded by the nucleotide sequences shown in FIG. 3C; and FIG. 3E is an alignment of the five light chains from the clone 27H5, wherein an asterisk (*) in the last row (labeled KEY) represents a conserved amino acid in that column; a colon (:) in the KEY row represents a conservative mutation; and a period (.) in the KEY row represents a semiconservative mutation.

FIGS. 4A, 4B, 4C, and 4D are a series of representations of the nucleotide sequence and amino acid sequences for the variable light and variable heavy regions of the huCD3 antibody 15C3, with FIG. 4A representing the nucleotide sequence encoding the variable region of the heavy chain, FIG. 4B representing the amino acid sequence encoded by the nucleotide sequence shown in FIG. 4A, FIG. 4C representing the two nucleotide sequences encoding the variable region of the light chain for the 15C3 clone, and FIG. 4D representing the two amino acid sequences encoded by the nucleotide sequences shown in FIG. 4C.

FIG. 5 is an alignment depicting the variable heavy chain regions of the 15C3, 27H5 and 28F11 huCD3 antibodies as well as the DP-50 germline sequence, the human heavy joining 5-02 sequence, and the human heavy joining 2 sequence. The CDR regions are indicated for each sequence.

FIG. 6 is an alignment depicting the VκIII variable regions of the 15C3 (variable light chain 1, i.e., "VL1") and 28F11 huCD3 antibodies, as well as the L6 germline sequence, the human kappa joining 4 sequence and the human kappa joining 1 sequence. The CDR regions are indicated for each sequence.

FIG. 7 is an alignment depicting the VκI variable regions of the 15C3 (variable light chain 2, i.e., "VL2") and 27H5 VL2 huCD3 antibodies, as well as the L4/18a germline sequence, the human kappa joining 4 sequence and the human kappa joining 5 sequence. The CDR regions are indicated for each sequence.

FIG. 8 is an alignment depicting the VκII variable regions of the 27H5 VL1 huCD3 antibody and DPK22, as well as human kappa joining 5 sequence. The CDR regions are indicated for each sequence.

FIG. 11A depicts the level of TNF-alpha release upon exposure to these antibodies, and FIG. 11B depicts the level of interferon gamma release.

DETAILED DESCRIPTION

Figure 9A:
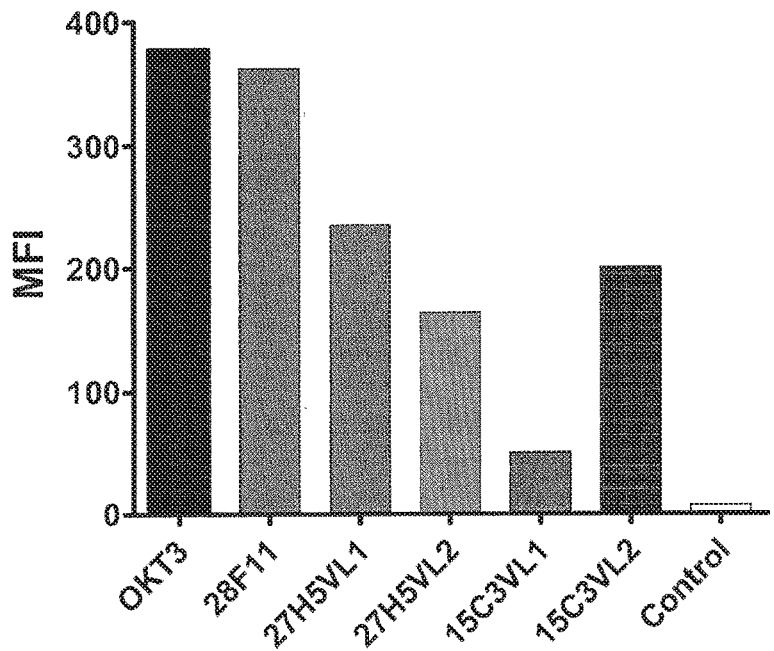
FIG. 9A is a graph depicting antibody binding to CD3 molecules at the surface of Jurkat cells using a variety of anti-CD3 antibodies, including the 28F11, 27H5VL1, 27H5VL2, 15C3VL1 and 15C3VL2 huCD3 antibodies of the invention.

The present invention provides fully human monoclonal antibodies specific against CD3 epsilon chain (CD3ϵ). The antibodies are respectively referred to herein is huCD3 antibodies.

CD3 is a complex of at least five membrane-bound polypeptides in mature T-lymphocytes that are non-covalently associated with one another and with the T-cell receptor. The CD3 complex includes the gamma, delta, epsilon, zeta, and eta chains (also referred to as subunits). Non-human monoclonal antibodies have been developed against some of these chains, as exemplified by the murine antibodies OKT3, SP34, UCHT1 or 64.1. (See e.g., Ledbetter, et al., J. Immunol. 136:3945-3952 (1986); Yang, et al., J. Immunol. 137:1097-1100 (1986); and Hayward, et al., Immunol. 64:87-92 (1988)).

The huCD3 antibodies of the invention were produced by immunizing two lines of transgenic mice, the HuMab™ mice and the KM™ mice (Medarex, Princeton N.J.).

The huCD3 antibodies of the invention have one or more of the following characteristics: the huCD3 antibody binds to CD3 positive (CD3+) cells but not CD3 negative (CD3−) cells; the huCD3 antibody induces antigenic modulation which involves alterations of the cell surface expression levels of CD3 and the T cell receptor (TcR); or the huCD3 antibody inhibits binding of the murine anti-human OKT3 monoclonal antibody to T-lymphocytes. The huCD3 antibodies of the invention compete with the murine anti-CD3 antibody OKT3 for binding to CD3, and exposure to the huCD3 antibody removes or masks CD3 and/or TcR without affecting cell surface expression of CD2, CD4 or CD8. The masking of CD3 and/or TcR results in the loss or reduction of T-cell activation.

The huCD3 antibodies of the invention bind to a CD3 that wholly or partially includes the amino acid residues from position 27 to position 43 of the processed human CD3 epsilon subunit (i.e., without the leader sequence). The amino acid sequence of the human CD3 epsilon subunit is shown, for example, in GenBank Accession Nos. NP_000724; AAA52295; P07766; A32069; CAA27516; and AAH49847. For example, the huCD3 antibody binds a CD3 epitope that wholly or partially includes the amino acid sequence of EMGGITQTPYKVSISGT (SEQ ID NO: 67). An exemplary huCD3 monoclonal antibody that binds to this epitope is the 28F11 antibody described herein. The 28F11 antibody includes a heavy chain variable region (SEQ ID NO:2) encoded by the nucleic acid sequence shown below in SEQ ID NO:1, and a light chain variable region (SEQ ID NO:4) encoded by the nucleic acid sequence shown in SEQ ID NO:3 (FIGS. 1A-1D).

The amino acids encompassing the complementarity determining regions (CDR) as defined by Chothia et al. 1989, E. A. Kabat et al., 1991 are highlighted with boxes below (see also FIGS. 1B and 1D and FIGS. 5 and 6). (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the 28F11 antibody have the following sequences: GYGMH (SEQ ID NO:27) VIWYDGSKKYYVDSVKG (SEQ ID NO:28) and QMGYWHFDL (SEQ ID NO:29). The light chain CDRs of the 28F11 antibody have the following sequences: RASQSVSSYLA (SEQ ID NO:30) DASNRAT (SEQ ID NO:31) and QQRSNWPPLT (SEQ ID NO:32).

```
>28F11 VH nucleotide sequence:
                                            (SEQ ID NO: 1)
CAGGTGCAGCTGGTGGAGTCCGGGGGAGGCGTGGTCCAGCCTGGGAGGTC

CCTGAGACTCTCCTGTGCAGCGTCTGGATTCAAGTTCAGTGGCTATGGCA

TGCACTGGGTCCGCCAGGCTCCAGGCAAGGGGCTGGAGTGGGTGGCAGTT

ATATGGTATGATGGAAGTAAGAAATACTATGTAGACTCCGTGAAGGGCCG

CTTCACCATCTCCAGAGACAATTCCAAGAACACGCTGTATCTGCAAATGA

ACAGCCTGAGAGCCGAGGACACGGCTGTGTATTACTGTGCGAGACAAATG

GGCTACTGGCACTTCGATCTCTGGGGCCGTGGCACCCTGGTCACTGTCTC

CTCA

>28F11 VH amino acid sequence:
                                            (SEQ ID NO: 2)
QVQLVESGGGVVQPGRSLRLSCAASGFKFS GYGMH WVRQAPGKGLEWVAV

IWYDGSKKYYVDSVKG RFTISRDNSKNTLYLQMNSLRAEDTAVYYCAR QM

GYWHFDL WGRGTLVTVSS

>28F11 VL nucleotide sequence:
                                            (SEQ ID NO: 3)
GAAATTGTGTTGACACAGTCTCCAGCCACCCTGTCTTTGTCTCCAGGGGA

AAGAGCCACCCTCTCCTGCAGGGCCAGTCAGAGTGTTAGCAGCTACTTAG

CCTGGTACCAACAGAAACCTGGCCAGGCTCCCAGGCTCCTCATCTATGAT

GCATCCAACAGGGCCACTGGCATCCCAGCCAGGTTCAGTGGCAGTGGGTC

TGGGACAGACTTCACTCTCACCATCAGCAGCCTAGAGCCTGAAGATTTTG

CAGTTTATTACTGTCAGCAGCGTAGCAACTGGCCTCCGCTCACTTTCGGC

GGAGGGACCAAGGTGGAGATCAAA

>28F11 VL amino acid sequence:
                                            (SEQ ID NO: 4)
EIVLTQSPATLSLSPGERATLSC RASQSVSSYLA WYQQKPGQAPRLLIY D

ASNRAT GIPARFSGSGSGTDFTLTISSLEPEDFAVYYC QQRSNWPPLT FG

GGTKVEIK
```

The 23F10 antibody includes a heavy chain variable region (SEQ ID NO:6) encoded by the nucleic acid sequence shown below in SEQ ID NO:5, and a light chain variable region (SEQ ID NO:8) encoded by the nucleic acid sequence shown in SEQ ID NO:7.

The amino acids encompassing the CDR as defined by Chothia et al. 1989, E. A. Kabat et al., 1991 are highlighted with boxes below. (see also FIGS. 2B, 2D). The heavy chain CDRs of the 23F10 antibody have the following sequences: GYGMH (SEQ ID NO:27) VIWYDGSKKYYVDSVKG (SEQ ID NO:28) and QMGYWHFDL (SEQ ID NO:29). The light chain CDRs of the 23F10 antibody have the following sequences: RASQSVSSYLA (SEQ ID NO:30) DASNRAT (SEQ ID NO:31) and QQRSNWPPLT (SEQ ID NO:32).

```
>23F10 VH nucleotide sequence:
                                         (SEQ ID NO: 5)
CAGGTGCAGCTGGTGCAGTCCGGGGGAGGCGTGGTCCAGTCTGGGAGGTC

CCTGAGACTCTCCTGTGCAGCGTCTGGATTCAAGTTCAGTGGCTATGGCA

TGCACTGGGTCCGCCAGGCTCCAGGCAAGGGGCTGGAGTGGGTGGCAGTT

ATATGGTATGATGGAAGTAAGAAATACTATGTAGACTCCGTGAAGGGCCG

CTTCACCATCTCCAGAGACAATTCCAAGAACACGCTGTATCTGCAAATGA

ACAGCCTGAGAGGCGAGGACACGGCTGTGTATTACTGTGCGAGACAAATG

GGCTACTGGCACTTCGATCTCTGGGGCCGTGGCACCCTGGTCACTGTCTC

CTCA

>23F10 VH amino acid sequence:
                                         (SEQ ID NO: 6)
QVQLVQSGGGVVQSGRSLRLSCAASGFKFSGYGMHWVRQAPGKGLEWVAV

IWYDGSKKYYVDSVKGRFTISRDNSKNTLYLQMNSLRGEDTAVYYCARQM

GYWHFDLWGRGTLVTVSS

>23F10 VL nucleotide sequence:
                                         (SEQ ID NO: 7)
GAAATTGTGTTGACACAGTCTCCAGCCACCCTGTCTTTGTCTCCAGGGGA

AAGAGCCACCCTCTCCTGCAGGGCCAGTCAGAGTGTTAGCAGCTACTTAG

CCTGGTACCAACAGAAACCTGGCCAGGCTCCCAGGCTCCTCATCTATGAT

GCATCCAACAGGGCCACTGGCATCCCAGCCAGGTTCAGTGGCAGTGGGTC

TGGGACAGACTTCACTCTCACCATCAGCAGCCTAGAGCCTGAAGATTTTG

CAGTTTATTACTGTCAGCAGCGTAGCAACTGGCCTCCGCTCACTTTCGGC

GGAGGGACCAAGGTGGAGATCAAA

>23F10 VL amino acid sequence:
                                         (SEQ ID NO: 8)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPPLTFG

GGTKVEIK
```

The 27H5 antibody includes a heavy chain variable region (SEQ ID NO:10) encoded by the nucleic acid sequence shown below in SEQ ID NO:9, and a light chain variable region selected from the amino acid sequences shown below in SEQ ID NOS: 16-20 and encoded by the nucleic acid sequences shown in SEQ ID NO:11-15. As described herein in Example 2, a single clonal hybridoma derived from the HuMAb® transgenic mice can produce multiple light chains for a single heavy chain. Each combination of heavy and light chains produced is tested for optimal functioning, as described herein in Example 2.

The amino acids encompassing the CDR as defined by Chothia et al. 1989, E. A. Kabat et al., 1991 are highlighted with boxes below. (see also FIGS. 3B, 3D, 5, and 7-8). The heavy chain CDRs of the 27H5 antibody have the following sequences: SYGMH (SEQ ID NO:33) IIWYDGSKKNY-ADSVKG (SEQ ID NO:34) and GTGYNWFDP (SEQ ID NO:35). The light chain CDRs of the 27H5 antibody have the following sequences: RASQSVSSSYLA (SEQ ID NO:36); GASSRAT (SEQ ID NO:37); QQYGSSPIT (SEQ ID NO:38); RASQGISSALA (SEQ ID NO:39); YASSLQS (SEQ ID NO:40); QQYYSTLT (SEQ ID NO:41); DASS-LGS (SEQ ID NO:42); and WASQGISSYLA (SEQ ID NO:43).

```
>27H5 VH nucleotide sequence:
                                         (SEQ ID NO: 9)
CAGGTGCAGCTGGTGGAGTCCGGGGGAGGCGTGGTCCAGCCTGGGAGGTC

CCTGAGACTCTCCTGTGCAGCGTCTGGATTCACCTTCAGAAGCTATGGCA

TGCACTGGGTCCGCCAGGCTCCAGGCAAGGGGCTGGAGTGGGTGGCAATT

ATATGGTATGATGGAAGTAAAAAAAACTATGCAGACTCCGTGAAGGGCCG

ATTCACCATCTCCAGAGACAATTCCAAGAACACGCTGTATCTGCAAATGA

ACAGCCTGAGAGCCGAGGACACGGCTGTGTATTACTGTGCGAGAGGAACT

GGGTACAACTGGTTCGACCCCTGGGGCCAGGGAACCCTGGTCACCGTCTC

CTCA

>27H5 VH amino acid sequence:
                                         (SEQ ID NO: 10)
QVQLVESGGGVVQPGRSLRLSCAASGFTFRSYGMHWVRQAPGKGLEWVAI

IWYDGSKKNYADSVKGRFTISRDNSKNTLYLQMNSLRAEDTAVYYCARGT

GYNWFDPWGQGTLVTVSS

>27H5 VL1 nucleotide sequence:
                                         (SEQ ID NO: 11)
GAAATTGTGTTGACACAGTCTCCACGCACCCTGTCTTTGTCTCCAGGGGA

AAGAGCCACCCTCTCCTGCAGGGCCAGTCAGAGTGTTAGCAGCAGCTACT

TAGCCTGGTACCAGCAGAAACCTGGCCAGGCTCCCAGGCTCCTCATCTAT

GGTGCATCCAGCAGGGCCACTGGCATCCCAGACAGGTTCAGTGGCAGTGG

GTCTGGGACAGACTTCACTCTCACCATCAGCAGACTGGACCCTGAAGATT

TTGCAGTGTATTACTGTCAGCAGTATGGTAGCTCACCGATCACCTTCGGC

CAAGGGACACGACTGGAGATTAAA

>27H5 VL2 nucleotide sequence:
                                         (SEQ ID NO: 12)
GACATCCTGATGACCCAGTCTCCATCCTCCCTGTCTGCATCTGTAGGAGA

CAGAGTCACCATCACTTGCCGGGCAAGTCAGGGCATTAGCAGTGCTTTAG

CCTGGTATCAGCAGAAACCAGGGAAAGCTCCTAAGCTCCTGATCTATTAT

GCATCCAGTTTGCAAAGTGGGGTCCCATCAAGGTTCAGCGGCAGTGGATC

TGGGACGGATTACACTCTCACCATCAGCAGCCTGCAGCCTGAAGATTTTG

CAACTTATTACTGTCAACAGTATTATAGTACCCTCACTTTCGGCGGAGGG

ACCAAGGTGGAGATCAAA
```

>27H5 VL3 nucleotide sequence:
(SEQ ID NO: 13)
GACATCGTGATGACCCAGTCTCCATCCTCCCTGTCTGCATCTGTAGGAGA

CAGAGTCACCATCACTTGCCGGGCAAGTCAGGGCATTAGCAGTGCTTTAG

CCTGGTATCAGCAGAAACCAGGGAAAGCTCCTAAGCTCCTGATCTATGAT

GCCTCCAGTTTGGGAAGTGGGGTCCCATCAAGGTTCAGCGGCAGTGGATC

TGGGACAGATTTCACTCTCACCATCAGCAGCCTGCAGCCTGAAGATTTTG

CAACTTATTACTGTCAACAGTATTATAGTACCCTCACTTTCGGCGGAGGG

ACCAAGGTGGAGATCAAA

>27H5 VL4 nucleotide sequence:
(SEQ ID NO: 14)
GACATCCAGATGACCCAGTCTCCATTCTCCCTGTCTGCATCTGTAGGAGA

CAGAGTCACCATCACTTGCTGGGCCAGTCAGGGCATTAGCAGTTATTTAG

CCTGGTATCAGCAAAAACCAGCAAAAGCCCCTAAGCTCTTCATCTATTAT

GCATCCAGTTTGCAAAGTGGGGTCCCATCAAGGTTCAGCGGCAGTGGATC

TGGGACGGATTACACTCTCACCATCAGCAGCCTGCAGCCTGAAGATTTTG

CAACTTATTACTGTCAACAGTATTATAGTACCCTCACTTTCGGCGGAGGG

ACCAAGGTGGAGATCAAA

>27H5 VL5 nucleotide sequence:
(SEQ ID NO: 15)
GACATCGAGATGACCCAGTCTCCATTCTCCCTGTCTGCATCTGTAGGAGA

CAGAGTCACCATCACTTGCTGGGCCAGTCAGGGCATTAGCAGTTATTTAG

CCTGGTATCAGCAAAAACCAGCAAAAGCCCCTAAGCTCTTCATCTATTAT

GCATCCAGTTTGCAAAGTGGGGTCCCATCAAGGTTCAGCGGCAGTGGATC

TGGGACGGATTACACTCTCACCATCAGCAGCCTGCAGCCTGAAGATTTTG

CAACTTATTACTGTCAACAGTATTATAGTACCCTCACTTTCGGCGGAGGG

ACCAAGGTGGAGATCAAA

>27H5 VL1 amino acid sequence:
(SEQ ID NO: 16)
EIVLTQSPRTLSLSPGERATLSC RASQSVSSYLA WYQQKPGQAPRLLIY

GASSRAT GIPDRFSGSGSGTDFTLTISRLDPEDFAVYYC QQYGSSPIT FG

QGTRLEIK

>27H5 VL2 amino acid sequence:
(SEQ ID NO: 17)
DILMTQSPSSLSASVGDRVTITC RASQGISSALA WYQQKPGKAPKLLIY Y

ASSLQS GVPSRFSGSGSGTDYTLTISSLQPEDFATYYC QQYYSTLT FGGG

TKVEIK

>27H5 VL3 amino acid sequence:
(SEQ ID NO: 18)
DIVMTQSPSSLSASVGDRVTITC RASQGISSALA WYQQKPGKAPKLLIY D

ASSLGS GVPSRFSGSGSGTDFTLTISSLQPEDFATYYC QQYYSTLTF GGG

TKVEIK

>27H5 VL4 amino acid sequence:
(SEQ ID NO: 19)
DIQMTQSPFSLSASVGDRVTITC WASQGISSYLA WYQQKPAKAPKLFIY Y

ASSLQS GVPSRFSGSGSGTDYTLTISSLQPEDFATYYC QQYYSTLTF GGG

TKVEIK

>27H5 VL5 amino acid sequence:
(SEQ ID NO: 20)
DIEMTQSPFSLSASVGDRVTITC WASQGISSYLA WYQQKPAKAPKLFIY Y

ASSLQS GVPSRFSGSGSGTDYTLTISSLQPEDFATYYC QQYYSTLTF GGG

TKVEIK

The 15C3 antibody includes a heavy chain variable region (SEQ ID NO:22) encoded by the nucleic acid sequence shown below in SEQ ID NO:21, and a light chain variable region selected from the amino acid sequences shown below in SEQ ID NOS: 25-26 and encoded by the nucleic acid sequences shown in SEQ ID NO:23-24. As described herein in Example 2, a single clonal hybridoma derived from the HuMAb® transgenic mice can produce multiple light chains for a single heavy chain. Each combination of heavy and light chains produced is tested for optimal functioning, as described herein in Example 2.

The amino acids encompassing the CDR as defined by Chothia et al. 1989, E. A. Kabat et al., 1991 are highlighted with boxes below. (see also FIGS. 4B, 4D, and 5-7). The heavy chain CDRs of the 15C3 antibody have the following sequences: SYGMH (SEQ ID NO:33) AIWYNGRKQDY-ADSVKG (SEQ ID NO:44) and GTGYNWFDP (SEQ ID NO:35). The light chain CDRs of the 15C3 antibody have the following sequences: RASQSVSSYLA (SEQ ID NO:30); DASNRAT (SEQ ID NO:31); QQRSNWPWT (SEQ ID NO:45); RASQGISSALA (SEQ ID NO:39); DASSLES (SEQ ID NO:46); QQFNSYPIT (SEQ ID NO:47).

>15C3 VH nucleotide sequence:
(SEQ ID NO: 21)
CAGGTGCAGCTGGTGCAGTCTGGGGGAGGCGTGGTCCAGCCCGGGAGGTC

CCTGAGACTCTCCTGTGTAGCGTCTGGATTCACCTTCAGTAGCTATGGCA

TGCACTGGGTCCGCCAGGCTCCAGGCAAGGGGCTGGAGTGGGTGGCAGCT

ATATGGTATAATGGAAGAAAACAAGACTATGCAGACTCCGTGAAGGGCCG

ATTCACCATCTCCAGAGACAATTCCAAGAACACGCTGTATCTGCAAATGA

ACAGCCTGAGAGCCGAGGACACGGCTGTGTATTACTGTACGAGGGGAACT

GGGTACAATTGGTTCGACCCCTGGGGCCAGGGAACCCTGGTCACCGTCTC

CTCA

>15C3 VH amino acid sequence:
(SEQ ID NO: 22)
QVQLVQSGGGVVQPGRSLRLSCVASGFTFS SYGMH WVRQAPGKGLEWVA A

IWYNGRKQDYADSVKG RFTISRDNSKNTLYLQMNSLRAEDTAVYYCTR GT

GYNWFDP WGQGTLVTVSS

>15C3 VL1 nucleotide sequence:
(SEQ ID NO: 23)
GAAATTGTGTTGACACAGTCTCCAGCCACCCTGTCTTTGTCTCCAGGGGA -continued

```
AAGAGCCACCCTCTCCTGCAGGGCCAGTCAGAGTGTTAGCAGCTACTTAG

CCTGGTACCAACAGAAACCTGGCCAGGCTCCCAGGCTCCTCATCTATGAT

GCATCCAACAGGGCCACTGGCATCCCAGCCAGGTTCAGTGGCAGTGGGTC

TGGGACAGACTTCACTCTCACCATCAGCAGCCTAGAGCCTGAAGATTTTG

CAGTTTATTACTGTCAGCAGCGTAGCAACTGGCCGTGGACGTTCGGCCAA

GGGACCAAGGTGGAAATCAAA

>15C3 VL2 nucleotide sequence:
                                          (SEQ ID NO: 24)
GCCATCCAGTTGACCCAGTCTCCATCCTCCCTGTCTGCATCTGTATGAGA

CAGAGTCACCATCACTTGCCGGGCAAGTCAGGGCATTAGCAGTGCTTTAG

CCTGGTATCAGCAGAAACCAGGGAAAGCTCCTAAGCTCCTGATCTATGAT

GCCTCCAGTTTGGAAAGTGGGGTCCCATCAAGGTTCAGCGGCAGTGGATC

TGGGACAGATTTCACTCTCACCATCAGCAGCCTGCAGCCTGAAGATTTTG

CAACTTATTACTGTCAACAGTTTAATAGTTACCCTATCACCTTCGGCCAA

GGGACACGACTGGAGATTAAA

>15C3 VL1 amino acid sequence:
                                          (SEQ ID NO: 25)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPWTFGQ

GTKVEIK

>15C3 VL2 amino acid sequence:
                                          (SEQ ID NO: 26)
AIQLTQSPSSLSASVGDRVTITCRASQGISSALAWYQQKPGKAPKLLIYD

ASSLESGVPSRFSGSGSGTDFTLTISSLQPEDFATYYCQQFNSYPITFGQ

GTRLEIK
``` huCD3 antibodies of the invention also include antibodies that include a heavy chain variable amino acid sequence that is at least 90%, 92%, 95%, 97% 98%, 99% or more identical the amino acid sequence of SEQ ID NO:2, 6, 10 or 22 and/or a light chain variable amino acid that is at least 90%, 92%, 95%, 97% 98%, 99% or more identical the amino acid sequence of SEQ ID NO:4, 8, 16-20 or 25-26.

Alternatively, the monoclonal antibody is an antibody that binds to the same epitope as 28F11, 27H5, 23F10 or 15C3.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. By "specifically bind" or "immunoreacts with" is meant that the antibody reacts with one or more antigenic determinants of the desired antigen and does not react (i.e., bind) with other polypeptides or binds at much lower affinity ($K_d$>$10^{-6}$) with other polypeptides.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ea., 2nd ed. Raven Press, N.Y. (1989)). The variable regions of each light/heavy chain pair form the antibody binding site.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia &Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 µM; preferably ≤100 nM and most preferably ≤10 nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides are quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to a CD3 epitope when the equilibrium binding constant ($K_d$) is ≤1 µM, preferably ≤100 nM, more preferably ≤10 nM, and most preferably ≤100 µM to about 1 pM, as measured by assays such as radioligand binding assays or similar assays known to those skilled in the art.

Those skilled in the art will recognize that it is possible to determine, without undue experimentation, if a human monoclonal antibody has the same specificity as a human monoclonal antibody of the invention (e.g., monoclonal antibody 28F11, 27H5, 23F10 or 15C3) by ascertaining whether the former prevents the latter from binding to a CD3 antigen polypeptide. If the human monoclonal antibody being tested competes with a human monoclonal antibody of the invention, as shown by a decrease in binding by the human monoclonal antibody of the invention, then the two monoclonal antibodies bind to the same, or a closely related, epitope. Another way to determine whether a human monoclonal antibody has the specificity of a human monoclonal antibody of the invention is to pre-incubate the human monoclonal antibody of the invention with the CD3 antigen polypeptide with which it is normally reactive, and then add the human monoclonal antibody being tested to determine if the human monoclonal antibody being tested is inhibited in its ability to bind the CD3 antigen polypeptide. If the human monoclonal antibody being tested is inhibited then, in all likelihood, it has the same, or functionally equivalent, epitopic specificity as the monoclonal antibody of the invention.

Various procedures known within the art are used for the production of the monoclonal antibodies directed against a protein such as a CD3 protein, or against derivatives, fragments, analogs homologs or orthologs thereof. (See, e.g., Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the entire sequence of both the light chain and the heavy chain, including the CDRs, arise from human genes. Such antibodies are termed "human antibodies", or "fully human antibodies" herein. Human monoclonal antibodies are prepared, for example, using the procedures described below in Example 1. Human monoclonal antibodies can be also prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

It is desirable to modify the antibody of the invention with respect to effector function, so as to enhance, e.g., the effectiveness of the antibody in treating immune-related diseases. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also includes $F_v$, $F_{ab}$, $F_{ab'}$ and $F_{(ab')2}$ huCD3 fragments, single chain huCD3 antibodies, bispecific huCD3 antibodies and heteroconjugate huCD3 antibodies.

Bispecific antibodies are antibodies that have binding specificities for at least two different antigens. In the present case, one of the binding specificities is for CD3. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling is accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding is achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio)propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS(N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Preferred polypeptides in accordance with the invention comprise the human heavy chain immunoglobulin molecules represented by FIGS. 1B, 2B, 3B and 4B and the human light chain immunoglobulin molecules represented by FIGS. 1D, 2D, 3D and 4D, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes Oligonucleotides linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid sequence comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

Similarly, unless specified otherwise, the lefthand end of single-stranded polynucleotide sequences is the 5' end the lefthand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long' more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to CD3, under suitable binding conditions, (2) ability to block appropriate CD3 binding, or (3) ability to inhibit CD3-expressing cell growth in vitro or in vivo. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drus with properties analogous to those of the template peptide. These types of non-peptide compound are termed "peptide mimetics" or "peptidomimetics". Fauchere, J. Adv. Drug Res. 15:29 (1986), Veber and Freidinger TINS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH$_2$NH—, —CH$_2$S—, —CH$_2$—CH$_2$—, —CH=CH—(cis and trans), —COCH$_2$—, CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I) fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects.

Human Antibodies and Humanization of Antibodies

A huCD3 antibody is generated, for example, by immunizing xenogenic mice capable of developing fully human antibodies (see Example 1). An IgG huCD3 antibody is generated, for example, by converting an IgM anti-CD3 antibody produced by a transgenic mouse (see Example 2). Alternatively, such a huCD3 antibody is developed, for example, using phase-display methods using antibodies containing only human sequences. Such approaches are well-known in the art, e.g., in WO92/01047 and U.S. Pat. No. 6,521,404, which are hereby incorporated by reference. In this approach, a combinatorial library of phage carrying random pairs of light and heavy chains are screened using natural or recombinant source of CD3 or fragments thereof.

This invention includes methods to produce a huCD3 antibody by a process wherein at least one step of the process includes immunizing a transgenic, non-human animal with human CD3 protein. Some of the endogenous heavy and/or kappa light chain loci of this xenogenic non-human animal have been disabled and are incapable of the rearrangement required to generate genes encoding immunoglobulins in response to an antigen. In addition, at least one human heavy chain locus and at least one human light chain locus have been stably transfected into the animal. Thus, in response to an administered antigen, the human loci rearrange to provide genes encoding human variable regions immunospecific for the antigen. Upon immunization, therefore, the xenomouse produces B-cells that secrete fully human immunoglobulins.

A variety of techniques are well-known in the art for producing xenogenic non-human animals. For example, see U.S. Pat. No. 6,075,181 and No. 6,150,584. By one strategy, the xenogeneic (human) heavy and light chain immunoglobulin genes are introduced into the host germ line (e.g., sperm or oocytes) and, in separate steps, the corresponding host genes are rendered non-functional by inactivation using homologous recombination. Human heavy and light chain immunoglobulin genes are reconstructed in an appropriate eukaryotic or prokaryotic microorganism, and the resulting DNA fragments are introduced into the appropriate host, for example, the pronuclei of fertilized mouse oocytes or embryonic stem cells. Inactivation of the endogenous host immunoglobulin loci is achieved by targeted disruption of the appropriate loci by homologous recombination in the host cells, particularly embryonic stem cells or pronuclei of fertilized mouse oocytes. The targeted disruption can involve introduction of a lesion or deletion in the target locus, or deletion within the target locus accompanied by insertion into the locus, e.g., insertion of a selectable marker. In the case of embryonic stem cells, chimeric animals are generated which are derived in part from the modified embryonic stem cells and are capable of transmitting the genetic modifications through the germ line. The mating of hosts with introduced human immunoglobulin loci to strains with inactivated endogenous loci will yield animals whose antibody production is purely xenogeneic, e.g., human.

In an alternative strategy, at least portions of the human heavy and light chain immunoglobulin loci are used to replace directly the corresponding endogenous immunoglobulin loci by homologous recombination in embryonic stem cells. This results in simultaneous inactivation and replacement of the endogenous immunoglobulin. This is followed by the generation of chimeric animals in which the embryonic stem cell-derived cells can contribute to the germ lines.

For example, a B cell clone that expresses human anti-CD3 antibody is removed from the xenogenic non-human animal and immortalized according to various methods known within the art. Such B cells may be derived directly from the blood of the animal or from lymphoid tissues, including but not restricted to spleen, tonsils, lymph nodes, and bone marrow. The resultant, immortalized B cells may be expanded and cultured in vitro to produce large, clinically applicable quantities of huCD3 antibody. Alternatively, genes encoding the immunoglobulins with one or more human variable regions can be recovered and expressed in a differing cell type, including but not restricted to a mammalian cell culture system, in order to obtain the antibodies directly or individual chains thereof, composed of single chain $F_v$ molecules.

In addition, the entire set of fully human anti-CD3 antibodies generated by the xenogenic non-human animal may be screened to identify one such clone with the optimal characteristics. Such characteristics include, for example, binding affinity to the human CD3 protein, stability of the interaction as well as the isotype of the fully human anti-CD3 antibody. Clones from the entire set which have the desired characteristics then are used as a source of nucleotide sequences encoding the desired variable regions, for further manipulation to generate antibodies with the-se characteristics, in alternative cell systems, using conventional recombinant or transgenic techniques.

This general strategy was demonstrated in connection with generation of the first XenoMouse™ strains as published in 1994. See Green et al. Nature Genetics 7:13-21 (1994). This approach is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, filed Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430, 938, Apr. 27, 1995, Ser. No. 08/464, 584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759, 620, filed Dec. 3, 1996 and U.S. Pat. Nos. 6,162,963, 6,150,584, 6, 114,598, 6,075,181, and 5,939,598 and Japanese Patent Nos. 3 068 180 B2, 3 068 506 B2, and 3 068 507 B2. See also Mendez et al. Nature Genetics 15:146-156 (1997) and Green and Jakobovits J. Exp. Med.: 188:483-495 (1998). See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000.

In an alternative approach, others have utilized a "minilocus" approach. In the minilocus approach, an exogenous Ig locus is mimicked through the inclusion of pieces (individual genes) from the Ig locus. Thus, one or more VH genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877, 397, 5,874,299, and 6,255,458 each to Lonberg and Kay, U.S. Pat. Nos. 5,591, 669 and 6,023,010 to Krimpenfort and Berns, U.S. Pat. Nos. 5,612,205, 5,721,367, and 5,789,215 to Berns et al., and U.S. Pat. No. 5,643,763 to Choi and Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, 081161,739, filed Dec. 3, 1993, Ser. No. 08/165,699, filed Dec. 10, 1993, Ser. No. 08/209,741, filed Mar. 9, 1994. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996).

An advantage of the minilocus approach is the rapidity with which constructs including portions of the Ig locus can be generated and introduced into animals. Commensurately, however, a significant disadvantage of the minilocus approach is that, in theory, insufficient diversity is introduced through the inclusion of small numbers of V, D, and J genes. Indeed, the published work appears to support this concern. B-cell development and antibody production of animals produced through use of the minilocus approach appear stunted. Therefore, research surrounding the present invention has consistently been directed towards the introduction of large portions of the Ig locus in order to achieve greater diversity and in an effort to reconstitute the immune repertoire of the animals.

Kirin has also demonstrated the generation of human antibodies from mice in which, through microcell fusion, large pieces of chromosomes, or entire chromosomes, have been introduced. See European Patent Application Nos. 773 288 and 843 961.

Human anti-mouse antibody (HAMA) responses have led the industry to prepare chimeric or otherwise humanized antibodies. While chimeric antibodies have a human constant region and a immune variable region, it is expected that certain human anti-chimeric antibody (HACA) responses will be observed, particularly in chronic or multi-dose utilizations of the antibody. Thus, it would be desirable to provide fully human antibodies against CD3 in order to vitiate concerns and/or effects of HAMA or HACA response.

The production of antibodies with reduced immunogenicity is also accomplished via humanization and display techniques using appropriate libraries. It will be appreciated that murine antibodies or antibodies from other species can be humanized or primatized using techniques well known in the art. See e.g., Winter and Harris Immunol Today 14:43 46 (1993) and Wright et al. Crit, Reviews in Immunol. 12125-168 (1992). The antibody of interest may be engineered by recombinant DNA techniques to substitute the CH1, CH2, CH3, hinge domains, and/or the framework domain with the corresponding human sequence (See WO 92102190 and U.S. Pat. Nos. 5,530,101, 5,585,089, 5, 693,761, 5,693,792, 5,714,350, and 5,777,085). Also, the use of Ig cDNA for construction of chimeric immunoglobulin genes is known in the art (Liu et al. P.N.A.S. 84:3439 (1987) and J. Immunol. 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of immunological Interest, N.I.H. publication no. 91-3242. Human C region genes are readily available from known clones. The choice of isotype will be guided by the desired effecter functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, $F(ab')_2$ and Fab may be prepared by cleavage of the intact protein, e.g., by protease or chemical cleavage. Alternatively, a truncated gene is designed. For example, a chimeric gene encoding a portion of the $F(ab')_2$ fragment would include DNA sequences encoding the CH1 domain and hinge region of the H chain, followed by a translational stop codon to yield the truncated molecule.

Consensus sequences of H and L J regions may be used to design oligonucleotides for use as priers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL-31 sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g., SV-40 early promoter, (Okayama et al. Mol. Cell. Bio. 3:280 (1983)), Rous sarcoma virus LTR (Gorman et al. P.N.A.S. 79:6777 (1982)), and moloney murine leukemia virus LTR (Grosschedl et al. Cell 41:885 (1985)). Also, as will be appreciated, native Ig promoters and the like may be used.

Further, human antibodies or antibodies from other species can be generated through display type technologies, including, without limitation, phage display, retroviral display, ribosomal display, and other techniques, using techniques well known in the art and the resulting molecules can be subjected to additional maturation, such as affinity maturation, as such techniques are well known in the art. Wright and Harris, supra., Hanes and Plucthau PEAS USA 94:4937-4942 (1997) (ribosomal display), Parmley and Smith Gene 73:305-318 (1988) (phage display), Scott TIB5 17:241-245

(1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH; 10:80-8A (1992), and U.S. Pat. No. 5,733,743. If display technologies are utilized to produce antibodies that are not human, such antibodies can be humanized as described above.

Using these techniques, antibodies can be generated to CD3 expressing cells, CD3 itself, forms of CD3, epitopes or peptides thereof, and expression libraries thereto (See e.g., U.S. Pat. No. 5,703,057) which can thereafter be screened as described above for the activities described above.

Design and Generation of Other Therapeutics

In accordance with the present invention and based on the activity of the antibodies that are produced and characterized herein with respect to CD3, the design of other therapeutic modalities beyond antibody moieties is facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules.

For example, in connection with bispecific antibodies, bispecific antibodies can be generated that comprise (i) two antibodies one with a specificity to CD3 and another to a second molecule that are conjugated together, (ii) a single antibody that has one chain specific to CD3 and a second chain specific to a second molecule, or (iii) a single chain antibody that has specificity to CD3 and the other molecule. Such bispecific antibodies can be generated using techniques that are well known for example, in connection with (i) and (ii) See e.g., Fanger et al. Immunol Methods 4:72-81 (1994) and Wright and Harris, supra, and in connection with (iii) See e.g., Traunecker et al. Int. J. Cancer (Suppl.) 7:51-52 (1992). In each case, the second specificity can be made to the heavy chain activation receptors, including, without limitation, CD 16 or CD64 (See e.g., Deo et al. 18:127 (1997)) or CD89 (See e.g., Valerius et al. Blood 90:4485-4492 (1997)). Bispecific antibodies prepared in accordance with the foregoing would be likely to kill cells expressing CD3, and particularly those cells in which the CD3 antibodies of the invention are effective.

In connection with immunotoxins, antibodies can be modified to act as immunotoxins utilizing techniques that are well known in the art. See e.g., Vitetta Immunol Today 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in Cancer Chemotherapy and Biotherapy 655-686 (2d edition, Chafner and Longo, eds., Lippincott Raven (1996)). See also U.S. Pat. Nos. 4,681,581, 4,735,210, 5,101,827, 5,102,990 (RE 35,500), U.S. Pat. Nos. 5,648,471, and 5,697,902. Each of immunotoxins and radiolabeled molecules would be likely to kill cells expressing CD3, and particularly those cells in which the antibodies of the invention are effective.

In connection with the generation of therapeutic peptides, through the utilization of structural information related to CD3 and antibodies thereto, such as the antibodies of the invention or screening of peptide libraries, therapeutic peptides can be generated that are directed against CD3. Design and screening of peptide therapeutics is discussed in connection with Houghten et al. Biotechniques 13:412-421 (1992), Houghten PNAS USA 82:5131-5135 (1985), Pinalla et al. Biotechniques 13:901-905 (1992), Blake and Litzi-Davis BioConjugate Chem. 3:510-513 (1992). Immunotoxins and radio labeled molecules can also be prepared, and in a similar manner, in connection with peptidic moieties as discussed above in connection with antibodies. Assuming that the CD3 molecule (or a form, such as a splice variant or alternate form) is functionally active in a disease process, it will also be possible to design gene and antisense therapeutics thereto through conventional techniques. Such modalities can be utilized for modulating the function of CD3. In connection therewith the antibodies of the present invention facilitate design and use of functional assays related thereto. A design and strategy for antisense therapeutics is discussed in detail in International Patent Application No. WO 94/29444. Design and strategies for gene therapy are well known. However, in particular, the use of gene therapeutic techniques involving intrabodies could prove to be particularly advantageous. See e.g., Chen et al. Human Gene Therapy 5:595-601 (1994) and Marasco Gene Therapy 4:11-15 (1997). General design of and considerations related to gene therapeutics is also discussed in International Patent Application No. WO 97/38137.

Knowledge gleaned from the structure of the CD3 molecule and its interactions with other molecules in accordance with the present invention, such as the antibodies of the invention, and others can be utilized to rationally design additional therapeutic modalities. In this regard, rational drug design techniques such as X-ray crystallography, computer-aided (or assisted) molecular modeling (CAMM), quantitative or qualitative structure-activity relationship (QSAR), and similar technologies can be utilized to focus drug discovery efforts. Rational design allows prediction of protein or synthetic structures which can interact with the molecule or specific forms thereof which can be used to modify or modulate the activity of CD3. Such structures can be synthesized chemically or expressed in biological systems. This approach has been reviewed in Capsey et al. Genetically Engineered Human Therapeutic Drugs (Stockton Press, NY (1988)). Further, combinatorial libraries can be designed and synthesized and used in screening programs, such as high throughput screening efforts.

Therapeutic Administration and Formulations

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include a huCD3 antibody of the invention, are used to treat or alleviate a symptom associated with an immune-related disorder, such as, for example, an autoimmune disease or an inflammatory disorder.

Autoimmune diseases include, for example, Acquired Immunodeficiency Syndrome (AIDS, which is a viral disease with an autoimmune component), alopecia greata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barré syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Méniere's disease, mixed connective tissue disease, multiple sclerosis, myasthenia gravis, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjögren's syndrome, stiff-man syndrome, systemic lupus erythematosus, Takayasu arteritis, temporal arteritis/giant cell arteritis, ulcerative colitis, uveitis, vitiligo and Wegener's granulomatosis.

Inflammatory disorders, include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

In one embodiment, the huCD3 antibody compositions of the invention are administered in conjunction with a second agent such as, for example, GLP-1 or a beta cell resting compound (i.e., a compound that reduces or otherwise inhibits insulin release, such as potassium channel openers). Examples of suitable GLP-1 compounds are described in e.g., the published application U.S. 20040037826, and suitable beta cell resting compounds are described in published application U.S. 20030235583, each of which is hereby incorporated by reference in its entirety.

In another embodiment, the huCD3 antibody compositions used to treat an immune-related disorder are administered in combination with any of a variety of known anti-inflammatory and/or immunosuppressive compounds. Suitable known compounds include, but are not limited to methotrexate, cyclosporin A (including, for example, cyclosporin microemulsion), tacrolimus, corticosteroids, statins, interferon beta, Remicade (Infliximab), Enbrel (Etanercept) and Humira (Adalimumab).

For example, in the treatment of rheumatoid arthritis, the huCD3 antibody compositions of the invention can be co-administered with corticosteroids, methotrexate, cyclosporin A, statins, Remicade (Infliximab), Enbrel (Etanercept) and/or Humira (Adalimumab).

In the treatment of uveitis, the huCD3 antibody compositions can be administered in conjunction with, e.g., corticosteroids, methotrexate, cyclosporin A, cyclophosphamide and/or statins. Likewise, patients afflicted with a disease such as Crohn's Disease or psoriasis can be treated with a combination of a huCD3 antibody composition of the invention and Remicaid (Infliximab), and/or Humira (Adalimumab).

Patients with multiple sclerosis can receive a combination of a huCD3 antibody composition of the invention in combination with, e.g., glatiramer acetate (Copaxone), interferon beta-1a (Avonex), interferon beta-1a (Rebif), interferon beta-1b (Betaseron or Betaferon), mitoxantrone (Novantrone), dexamethasone (Decadron), methylprednisolone (Depo-Medrol), and/or prednisone (Deltasone) and/or statins.

The present invention also provides methods of treating or alleviating a symptom associated with an immune-related disorder or a symptom associated with rejection following organ transplantation. For example, the compositions of the invention are used to treat or alleviate a symptom of any of the autoimmune diseases and inflammatory disorders described herein.

The therapeutic compositions of the invention are also used as immunosuppression agents in organ or tissue transplantation. As used herein, "immunosuppression agent" refers to an agent whose action on the immune system leads to the immediate or delayed reduction of the activity of at least one pathway involved in an immune response, whether this response is naturally occurring or artificially triggered, whether this response takes place as part of the innate immune system, the adaptive immune system, or both. These immunosuppressive huCD3 antibody compositions are administered to a subject prior to, during and/or after organ or tissue transplantation. For example, a huCD3 antibody of the invention is used to treat or prevent rejection after organ or tissue transplantation.

In one embodiment, the immunosuppressive huCD3 antibody compositions of the invention are administered in conjunction with a second agent such as, for example, GLP-1 or a beta cell resting compound, as described above.

In another embodiment, these immunosuppressive huCD3 antibody compositions are administered in combination with any of a variety of known anti-inflammatory and/or immunosuppressive compounds. Suitable anti-inflammatory and/or immunosuppressive compounds for use with the huCD3 antibodies of the invention include, but are not limited to, methotrexate, cyclosporin A (including, for example, cyclosporin microemulsion), tacrolimus, corticosteroids and statins.

In yet another embodiment of the invention, a huCD3 antibody is administered to a human individual upon detection of the presence of auto-reactive antibodies within the human individual. Such auto-reactive antibodies are known within the art as antibodies with binding affinity to one or more proteins expressed endogenously within the human individual. In one aspect of the invention, the human individual is tested for the presence of auto-reactive antibodies specifically involved in one or more autoimmune diseases as are well known within the art. In one specific embodiment, a human patient is tested for the presence of antibodies against insulin, glutamic acid decarboxylase and/or the IA-2 protein, and subsequently administered with a huCD3 antibody upon positive detection of one or more such autoreactive antibodies.

In another embodiment of the invention, a huCD3 antibody is administered into human subjects to prevent, reduce or decrease the recruitment of immune cells into human tissues. A huCD3 antibody of the invention is administered to a subject in need thereof to prevent and treat conditions associated with abnormal or deregulated immune cell recruitment into tissue sites of human disease.

In another embodiment of the invention, a huCD3 antibody is administered into human subjects to prevent, reduce or decrease the extravasation and diapedesis of immune cells into human tissues. Thus, the huCD3 antibodies of the invention are administered to prevent and/or treat conditions associated with abnormal or deregulated immune cell infiltration into tissue sites of human disease.

In another embodiment of the invention, a huCD3 antibody is administered into human subjects to prevent, reduce or decrease the effects mediated by the release of cytokines within the human body. The term "cytokine" refers to all human cytokines known within the art that bind extracellular receptors upon the cell surface and thereby modulate cell function, including but not limited to IL-2, IFN-g, TNF-a, IL-4, IL-5, IL-6, IL-9, IL-10, and IL-13.

The release of cytokines can lead to a toxic condition known as the cytokine release syndrome (CRS), a common clinical complication that occurs, e.g., with the use of an anti-T cell antibody such as ATG (anti-thymocyte globulin) and OKT3 (a murine anti-human CD3 antibody). This syndrome is characterized by the excessive release of cytokines such as TNF, IFN-gamma and IL-2 into the circulation. The CRS occurs as a result of the simultaneous binding of the antibodies to CD3 (via the variable region of the antibody) and the Fc Receptors and/or complement receptors (via the constant region of the antibody) on other cells, thereby activating the T cells to release cytokines that produce a systemic inflammatory response characterized by hypotension, pyrexia and rigors. Symptoms of CRS include fever, chills, nausea, vomiting, hypotension, and dyspnea. Thus, a huCD3 antibody of the invention contains one or more mutations designed to prevent abnormal release and production of one or more cytokine(s) in vivo.

In another embodiment of the invention, a huCD3 antibody is administered into human subjects to prevent, reduce or decrease the effects mediated by the release of cytokine receptors within the human body. The term "cytokine receptor" refers to all human cytokine receptors within the art that bind one or more cytokine(s), as defined herein, including but not limited to receptors of the aforementioned cytokines. Thus, a huCD3 antibody of the invention is administered to treat and/or prevent conditions mediated through abnormal activation, binding or ligation of one or more cytokine receptor(s) within the human body. It is further envisioned that administration of the huCD3 antibody in vivo will deplete the intracellular signaling mediated by cytokine receptor(s) within such human subject.

In one aspect of the invention, a huCD3 antibody is administered to a human individual upon decrease of pancreatic beta-cell function therein. In one embodiment, the individual is tested for beta-cell function, insulin secretion or c-peptide levels as are known within the art. Subsequently, upon notice of sufficient decrease of either the indicator, the human individual is administered with a sufficient dosage regimen of a huCD3 antibody to prevent further progression of autoimmune destruction of beta-cell function therein.

Diagnostic and Prophylactic Formulations

The fully human anti-CD3 MAbs of the invention are used in diagnostic and prophylactic formulations. In one embodiment, a huCD3 MAb of the invention is administered to patients that are at risk of developing one of the aforementioned autoimmune diseases. A patient's predisposition to one or more of the aforementioned autoimmune diseases can be determined using genotypic, serological or biochemical markers. For example, the presence of particular HLA subtypes and serological autoantibodies (against insulin, GAD65 and IA-2) are indicative of Type I diabetes.

In another embodiment of the invention, a huCD3 antibody is administered to human individuals diagnosed with one or more of the aforementioned autoimmune diseases. Upon diagnosis, a huCD3 antibody is administered to mitigate or reverse the effects of autoimmunity. In one such example, a human individual diagnosed with Type I diabetes is administered with sufficient dose of a huCD3 antibody to restore pancreatic function and minimize damage of autoimmune infiltration into the pancreas. In another embodiment, a human individual diagnosed with rheumatoid arthritis is administered with a huCD3 antibody to reduce immune cell infiltration into and destruction of limb joints.

Antibodies of the invention are also useful in the detection of CD3 in patient samples and accordingly are useful as diagnostics. For example, the huCD3 antibodies of the invention are used in in vitro assays, e.g., ELISA, to detect CD3 levels in a patient sample.

In one embodiment, a huCD3 antibody of the invention is immobilized on a solid support (e.g., the well(s) of a microtiter plate). The immobilized antibody serves as a capture antibody for any CD3 that may be present in a test sample. Prior to contacting the immobilized antibody with a patient sample, the solid support is rinsed and treated with a blocking agent such as mink protein or albumin to prevent nonspecific adsorption of the analyte.

Subsequently the wells were treated with a test sample suspected of containing the antigen, or with a solution containing a standard amount of the antigen. Such a sample may be, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of CD3 antigen in the test sample is determined by comparison with a standard curve developed from the standard samples.

It will be appreciated that based on the results obtained using the huCD3 antibodies of the invention in an in vitro diagnostic assay, it is possible to stage a disease (e.g., an autoimmune or inflammatory disorder) in a subject based on expression levels of the CD3 antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following examples, including the experiments conducted and results achieved are provided for illustrative purposes only and are not to be construed as limiting upon the present invention.

Example 1

Generation of huCD3 Antibodies

Immunization Strategies: To generate a fully human huCD3 antibody, two lines of transgenic mice were utilized, the HuMab® mice and the KM™ mice (Medarex, Princeton N.J.). Initial immunization strategies followed well-documented protocols from the literature for generating mouse antibodies. (See e.g., Kung P, et al., Science; 206(4416): 347-9 (1979); Kung P C, et al., Transplant Proc. (3 Suppl 1):141-6 (1980); Kung P C, et al., Int J Immunopharmacol. 3(3):175-81 (1981)). The standard protocols known in the art failed to produce fully human anti-CD3 antibodies in the HuMAb® or the KM Mouse™. For example, the following immunization strategies were unsuccessful and did not produce functional antibodies in either the HuMAb® or KM Mice™:

immunization with thymocytes only or T-cells only
immunization with recombinant human CD3 material only
immunization with recombinant CD3 material in Freund's adjuvant
immunization with cell in Freund's adjuvant
immunization with thymocytes or T-cells co-administered with soluble CD3
immunization with thymocytes or T-cells co-administered with recombinant CD3-expressing cells When these prior art immunization strategies are used in a BALB/c mouse rather than a HuMab® or KM™ mouse, these strategies produce a murine anti-CD3 antibody rather than a human anti-CD3 antibody.

Accordingly, novel immunization strategies were developed by varying the following parameters:
types of immunogens employed
frequency of injection
types of adjuvants employed
types of co-stimulation techniques employed
routes of immunization employed
types of secondary lymphoid tissue used for fusion A series of novel immunization strategies were developed, including for example, (i) immunization with a viral particle expressing CD3 only, and (ii) immunization with co-stimulatory signals (e.g., CD40, CD27 or combinations thereof) co-administered with T cells, thymocytes, or with cells that have been transfected to express recombinant CD3.

In a first novel immunization strategy, referred to herein as the "hyper-boost protocol", a HuMAb® mouse (Medarex, Inc., Princeton, N.J.) or a KM™ mouse (Medarex, Inc., Kirin) was immunized by first injecting human cells, e.g., thymocytes or T-cells. At time points ranging from 1 to 8 weeks after injection of the thymocytes and/or T-cells, the mice received one or more subsequent "hyper-boost" injections. The hyper-boost injection included, for example, soluble CD3 protein (e.g., recombinant soluble CD3 protein), additional injections of thymocytes or T-cells, CD3-transfected cells, viral particles expressing high levels of CD3, and combinations thereof. For example, the hyper-boost injection contained a combination of soluble CD3 protein and CD3-transfected cells.

Preferably, in the hyper-boost immunization protocols, the immunized mice received two final hyper-boost injections at −6 and −3 days prior to fusion of the lymph nodes and/or spleen. For example, in the KM Mouse™, the fused tissue is derived from the spleen, and in the HuMAb® mouse, the fused tissue is derived from lymph nodes and/or splenic tissue.

In one example of the hyper-boost immunization protocol, one HuMAb™ mouse was immunized three times with human thymocytes (~$10^6$ cells) on days 0, 7 and 28. The Chinese ovarian cells line (CHO) transfected with the cDNA encoding human CD3 δ and ε chains (CHO/CD3, ~$10^6$ cells) was then injected on days 47 and 65. Another boost with a viral particle expressing high levels of CD3δε at its surface was given on day 79. Finally, the mouse was injected with soluble recombinant human CD3δε on day 121 and 124 before fusion of the lymph nodes on day 127.

All immunizations were given subcutaneously with Ribi (Corixa Corp., Seattle WA) as an adjuvant. A total of $8.5\times10^6$ cells were fused. Only seven out of 470 hybridomas screened produced a fully human anti-CD3 antibody, and all of the fully human anti-CD3 antibodies were IgM molecules. Two of these anti-CD3 antibodies were selected as therapeutic clinical candidates (FIGS. 1A, 1B, 1C, 1D, 2A, 2B, 2C, 2D, 3A, 3B, 3C, 3D and 3E).

In a second example of the hyper-boost immunization protocol, one KM™ mouse was immunized twice with soluble recombinant human CD3 δε on days 0 and 25. Human thymocytes (~$10^6$ cells) were then used for boosting on days 40, 49 and 56. The soluble recombinant CD3δε was injected twice on days 70, 77, 84 and 91. The mouse T cell line transfected with the cDNA encoding human CD3 δ and ε chains (EL4/CD3, ~$10^6$ cells) was then injected on day 98. Finally, the mouse was injected with soluble recombinant human CD3δε on day 101 before fusion of the spleen on day 104. Immunizations were administered intraperitoneally with Alum as an adjuvant, except on day 70 where Ribi adjuvant was used. CpG was used as a costimulatory agent on day 0, 25, 84 and 91. A total of $1.27\times10^8$ cells were fused. Only five out of 743 hybridomas screened produced a fully human anti-CD3 antibody, and all of antibodies produced were IgG molecules. One of the fully human anti-CD3 antibodies was selected as a therapeutic clinical candidate (FIGS. 4A, 4B, 4C, and 4D).

Figure 9B:
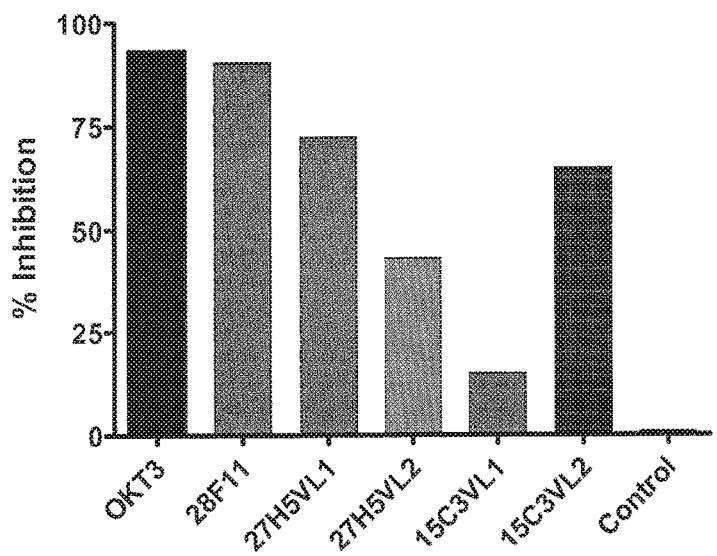
FIG. 9B is a graph depicting the ability of a variety of anti-CD3 antibodies, including the 28F11, 27H5VL1, 27H5VL2, 15C3VL1 and 15C3VL2 huCD3 antibodies of the invention, to inhibit the binding of the murine anti-CD3 antibody OKT3 to CD3 positive cells.
Figure 9C:
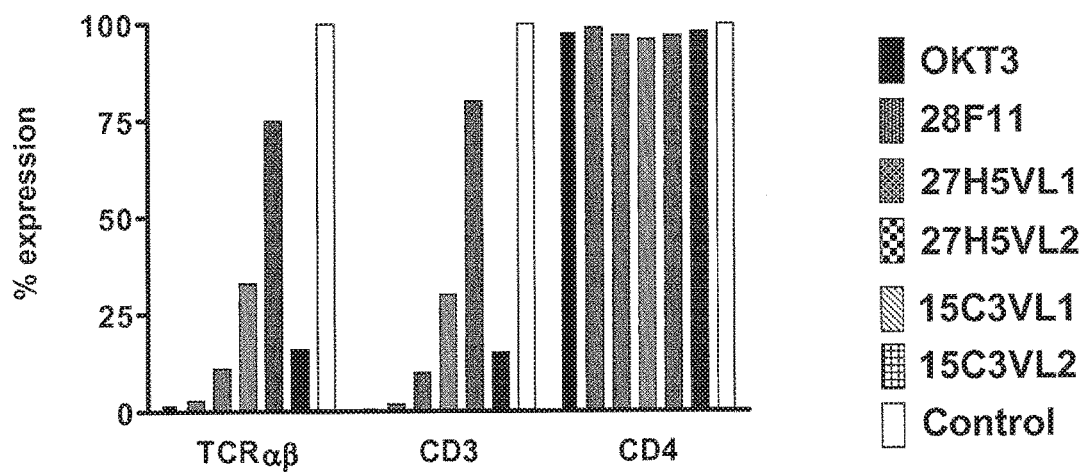
FIG. 9C is a graph depicting the antigenic modulation of CD3 and TCR from the surface of human peripheral blood T cells by a variety of anti-CD3 antibodies, including the 28F11, 27H5VL1, 27H5VL2, 15C3VL1 and 15C3VL2 huCD3 antibodies of the invention.
Figure 9D:
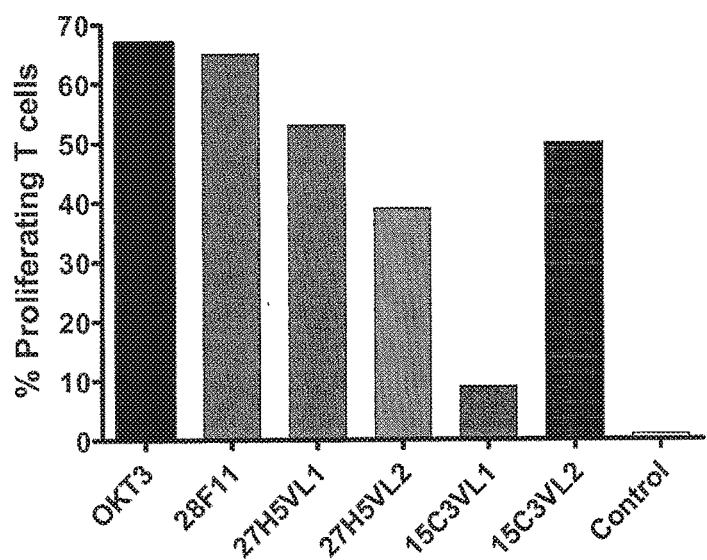
FIG. 9D is a graph depicting the effect of a variety anti-CD3 antibodies, including the 28F11, 27H5VL1, 27H5VL2, 15C3VL1 and 15C3VL2 huCD3 antibodies of the invention, on T-cell proliferation.

Selection Criteria: Therapeutic clinical candidates were selected using the following criteria. First, antibody-binding to CD3 positive cells versus CD3 negative cells was analyzed. For this, Jurkat CD3 positive cells (J+) and Jurkat negative cells (J−) were incubated with the different antibodies and binding was assessed by flow cytometry (FIG. 9A). Second, a competition assay in which the ability of the candidate antibody to inhibit the binding of the murine anti-human OKT3 monoclonal antibody to CD3 positive cells was assessed using J+ cells and competition was assessed by flow cytometry (FIG. 9B). Next, antigenic modulation of CD3 and the TCR from the surface of human peripheral blood T cells was assessed by flow cytometry (FIG. 9C). Finally, a T-cell proliferation assay was performed using human peripheral blood T cells dyed with CFSE and cell division was assessed by flow cytometry (FIG. 9D).

Example 2

Isotype Switching of Human Anti-CD3 Antibodies

Some huCD3 antibodies produced using the novel protocols described in Example 1 were IgM antibodies. These IgM antibodies were "converted" to an IgG antibody, preferably to an IgG1 antibody. For example, the IgM antibodies were converted by a cloning procedure in which the VDJ region of the gene encoding the IgM antibody was cloned into an IgG1 heavy chain gene obtained from a vector that contains a gene encoding allotype F gamma1. For conversion of the light chain, the IgM sequence was cloned into a vector containing the kappa region. In Medarex mice, e.g., the HuMAb® mouse, multiple light chains are produced, due to a lack of allelic exclusion.

Each combination of heavy and light chains was transfected into 293T cells using the FuGENE 6 (Roche Diagnostics) transfection agent according to the manufacturer's guidelines. The secreted monoclonal antibodies were tested for optimized functionality, e.g., target antigen binding, using the selection criteria described in Example 1.

Example 3

Antigenic Modulation Using the huCD3 Antibodies

The huCD3 antibodies of the invention are capable of antigenic modulation, which is defined as the redistribution and elimination of the CD3-TCR complex induced by antibody binding. Cell surface expression of other molecules on T cells, including, for example, CD4 is not altered by exposure to an anti-CD3 antibody of the invention (FIG. 9C).

Example 4

Reducing the Toxic Cytokine Release Syndrome Generated by huCD3 Antibodies

Preferably, the huCD3 antibodies of the invention include a mutation in the Fc region, such that the mutation alters cytokine release syndrome. As described above, the cytokine release syndrome (CRS) is a common immediate complication that occurs with the use of an anti-T cell antibody such as ATG (anti-thymocyte globulin) and OKT3 (a murine anti-CD3 antibody). This syndrome is characterized by the excessive release of cytokines such as TNF, IFN-gamma and IL-2 into the circulation. The cytokines released by the activated T cells produce a type of systemic inflammatory response similar to that found in severe infection characterized by hypotension, pyrexia and rigors. Symptoms of CRS include, for example, fever, chills, nausea, vomiting, hypotension, and dyspnea.

The huCD3 antibodies of the invention contain one or more mutations that prevent heavy chain constant region-mediated release of one or more cytokine(s) in vivo. In one embodiment, the huCD3 antibodies of the invention are IgG molecules having one or more of the following mutations in a modified IgG γ1 backbone: "γ1 N297A", in which the asparagine residue at position 297 is replaced with an alanine residue; "γ1 L234/A, L235/A", in which the leucine residues at positions 234 and 235 are replaced with alanine residues; "γ1 L234/A; L235/E", in which the leucine residue at position 234 is replaced with an alanine residue, while the leucine residue at position 235 is replaced with a glutamic acid residue; "γ1 L235/E" in which the leucine residue at position 235 is replaced with a glutamic acid residue; and "γ1 D265/A" in which the aspartic acid residue at position 265 is replaced with an alanine residue. The numbering of the heavy chain residues described herein is that of the EU index (see Kabat et al., "Proteins of Immunological Interest", US Dept. of Health & Human Services (1983)), as shown, e.g., in U.S. Pat. Nos. 5,624,821 and 5,648,260, the contents of which are hereby incorporated in its entirety by reference.

Other IgG γ1 backbone modifications that can be used in the huCD3 antibodies of the invention include, for example, "A330/S" in which the alanine residue at position 330 is replaced with a serine residue, and/or "P331/S" in which the proline residue at position 331 is replaced with a serine residue.

Figure 11A:
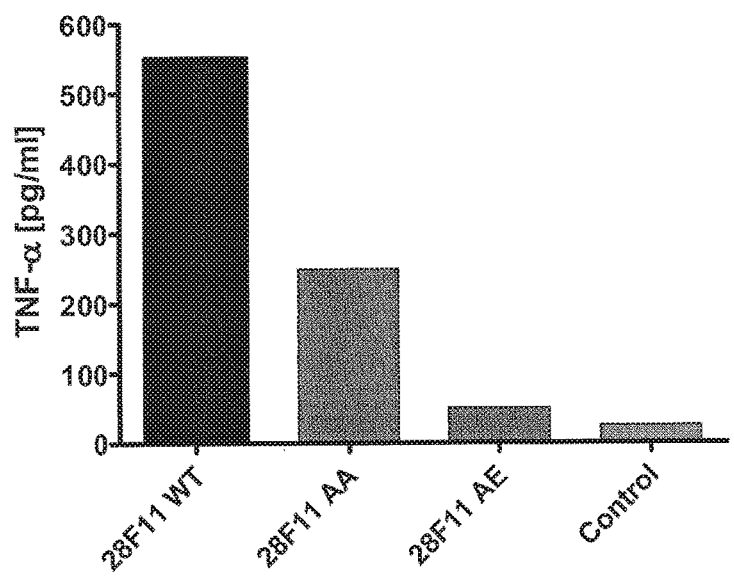
FIGS. 11A and 11B are a series of graphs depicting the level of cytokine release upon exposure to wild-type 28F11 huCD3 antibody (28F11WT), a mutated 28F11huCD3 antibody having a $L^{234} L^{235} \rightarrow A^{234} A^{235}$ mutation (28F11AA), and a mutated 28F11 huCD3antibody having a $L^{234} L^{235} \rightarrow A^{234} E^{235}$ mutation (28F11AE).
Figure 11B:
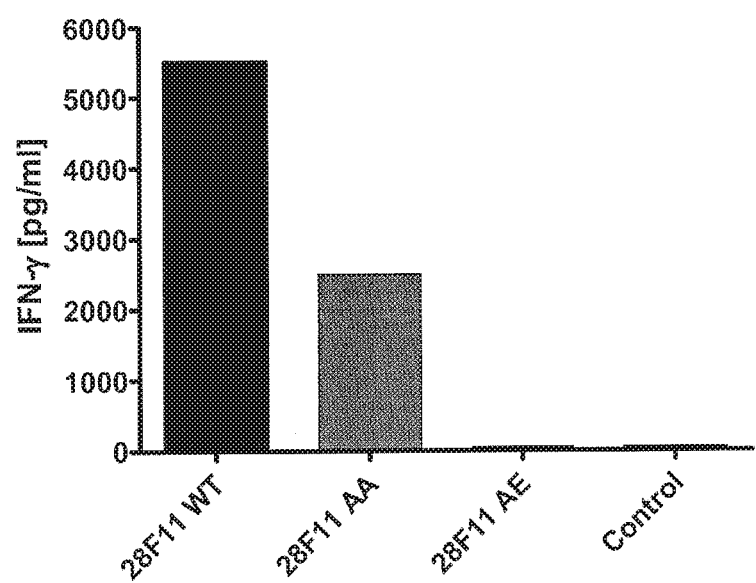

The fully human CD3 antibodies of the invention having a $L^{234} L^{235} \rightarrow A^{234} E^{235}$ mutation in the Fc region have a unique function—elimination of cytokine release in the presence of the huCD3 antibody. Prior studies have actually taught away from the use of an L→E mutation (see e.g., Xu et al., Cellular Immunology, 200, pp. 16-26 (2000), at p. 23). However, these particular two mutations at positions 234 and 235 (i.e., $L^{234} L^{235} \rightarrow A^{234} E^{235}$) eliminated the cytokine release syndrome, as assessed peripheral human blood mononuclear cell in vitro assay system (FIGS. 11A, 11B). In this assay, peripheral human blood mononuclear cells were isolated using a ficoll gradient, labeled with CFSE and the CFSE-labeled cells were then plated into 96 well plates. The various monoclonal antibodies were added at various dilutions and incubated for 72 hours at 37° C. After 6 hours, 50 μl of supernatant was removed to evaluate TNF release by ELISA. After 48 hours, 50 μl of supernatant was removed to evaluate IFN-γ release by ELISA. After 72 hours, the cells were harvested and proliferation was assessed by FACS using CFSE-labeling intensity.

Thus, contrary to wild type heavy chains, and contrary to a series of other mutations that had been described by others (e.g., TolerX (aglycosylation mutation), Bluestone ($L^{234} L^{235} \rightarrow A^{234} A^{235}$ mutation) (see e.g., U.S. Pat. No. 5,885, 573)), which all retain a significant level of cytokine release effect, the $L^{234} L^{235} \rightarrow A^{234} E^{235}$ mutations of the huCD3 antibodies of the invention do not exhibit cytokine release phenomenon. The level of remaining cytokine release effect was 100% for the wild type Fc, about 50 to 60% for the Bluestone ($L^{234} L^{235} \rightarrow A^{234} A^{235}$) mutation and undetectable for Ala/Glu Fc mutations described herein (FIG. 11A, 11B).

Example 5

Peptide Array Identification of the huCD3 Antibody-Binding Epitope

The synthesis and ELISA screening of large numbers of peptides have been used to determine the amino acid residues involved in the epitope for various monoclonal antibodies. (See e.g., Geysen et al., J Immunol Methods, vol. 102(2):259-74 (1987)). In the experiments described herein, arrays of overlapping peptides derived from the amino acid sequence of the CD3 epsilon chain were purchased from Jerini (Berlin, Germany) and subsequently tested for a pattern of binding by the fully human anti-CD3 mAbs of the invention.

Figure 10:
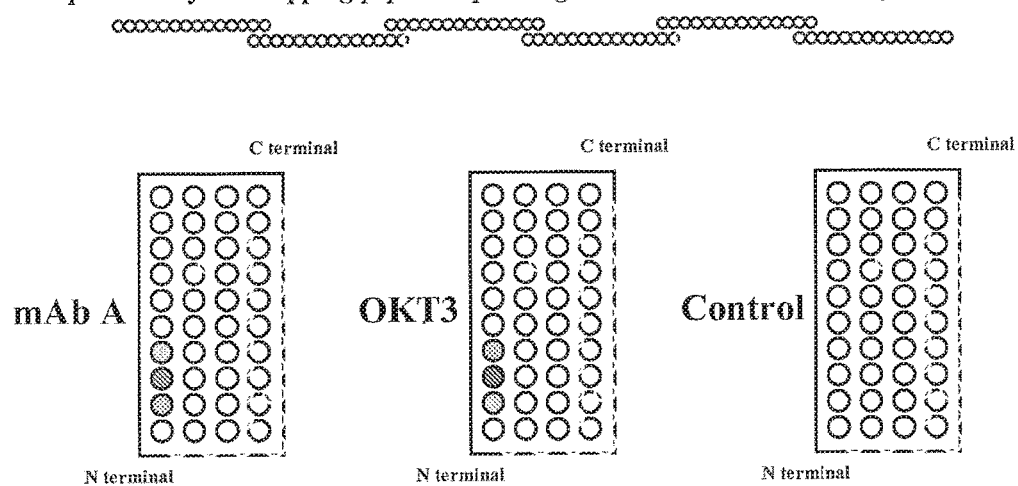
FIG. 10 is an illustration depicting the binding pattern of the fully human monoclonal antibody 28F11 on a peptide array derived from the amino acid sequence of the CD3 epsilon chain.

The peptides in the arrays were produced using the "SPOT synthesis" technique for direct chemical synthesis on membrane supports (see Frank and Overwin, Meth Mol Biol, vol. 66:149-169 (1996); Kramer and Schneider-Mergener, Meth Mol Biol, vol. 87:25-39 (1998)). The linear 14-mer peptides were covalently bound to a Whatman 50 cellulose support by the C-terminus, leaving the N-terminus free (i.e., unbound). Using standard western blotting techniques, these solid phase-bound peptides revealed that the 28F11 monoclonal recognized an overlapping set of amino acids in proximity to the N terminus (FIG. 10).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated fully human monoclonal antibody, wherein said antibody has a heavy chain with three complementarity determining regions (CDRs) comprising a VH CDR1 comprising the amino acid sequence SYGMH (SEQ ID NO:33); a VH CDR2 comprising the amino acid sequence of IIWYDGSKKNYADSVKG (SEQ ID NO:34); and a VH CDR3 comprising the amino acid sequence of GTGYN-WFDP (SEQ ID NO:35); and a light chain with three CDRs, comprising a VL CDR1 comprising the amino acid sequence of RASQSVSSSYLA (SEQ ID NO:36); a VL CDR2 comprising the amino acid sequence of GASSRAT (SEQ ID NO:37); and a VL CDR3 comprising the amino acid sequence of QQYGSSPIT (SEQ ID NO:38), wherein said antibody binds CD3.

2. The antibody of claim 1, wherein said antibody further comprises the heavy chain variable amino acid sequence of SEQ ID NO: 10, and the light chain variable amino acid sequence of SEQ ID NOS: NO: 16.

3. The antibody of claim 1, wherein said antibody is an IgG1 isotype.

* * * * *

SEQUENCE LISTING

```
<160> NUMBER OF SEQ ID NOS: 74

<210> SEQ ID NO 1
<211> LENGTH: 354
<212> TYPE: DNA
<213> ORGANISM: Homo sapiens

<400> SEQUENCE: 1
caggtgcagc tggtggagtc cggggggaggc gtggtccagc ctgggaggtc cctgagactc      60
tcctgtgcag cgtctggatt caagttcagt ggctatggca tgcactgggt ccgccaggct     120
ccaggcaagg ggctggagtg ggtggcagtt atatggtatg atggaagtaa gaaatactat     180
gtagactccg tgaagggccg cttcaccatc tccagagaca attccaagaa cacgctgtat     240
ctgcaaatga acagcctgag agccgaggac acggctgtgt attactgtgc gagacaaatg     300
ggctactggc acttcgatct ctggggccgt ggcaccctgg tcactgtctc ctca           354

<210> SEQ ID NO 2
<211> LENGTH: 118
<212> TYPE: PRT
<213> ORGANISM: Homo sapiens

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Lys Phe Ser Gly Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Met Gly Tyr Trp His Phe Asp Leu Trp Gly Arg Gly Thr
            100                 105                 110

Leu Val Thr Val Ser Ser
        115

<210> SEQ ID NO 3
<211> LENGTH: 324
<212> TYPE: DNA
<213> ORGANISM: Homo sapiens

<400> SEQUENCE: 3
gaaattgtgt tgacacagtc tccagccacc ctgtctttgt ctccagggga aagagccacc      60
```

```
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctccgct cactttcggc    300
ggagggacca aggtggagat caaa                                          324
```

<210> SEQ ID NO 4
<211> LENGTH: 108
<212> TYPE: PRT
<213> ORGANISM: Homo sapiens

<400> SEQUENCE: 4

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Thr Phe Gly Gly Gly Thr Lys Val Glu Ile Lys
            100                 105
```

<210> SEQ ID NO 5
<211> LENGTH: 354
<212> TYPE: DNA
<213> ORGANISM: Homo sapiens

<400> SEQUENCE: 5

```
caggtgcagc tggtgcagtc cggggggaggc gtggtccagt ctggggaggtc cctgagactc    60 tcctgtgcag cgtctggatt caagttcagt ggctatggca tgcactgggt ccgccaggct    120
ccaggcaagg ggctggagtg ggtggcagtt atatggtatg atggaagtaa gaaatactat    180
gtagactccg tgaagggccg cttcaccatc tccagagaca attccaagaa cacgctgtat    240
ctgcaaatga acagcctgag aggcgaggac acggctgtgt attactgtgc gagacaaatg    300
ggctactggc acttcgatct ctggggccgt ggcaccctgg tcactgtctc ctca          354
```

<210> SEQ ID NO 6
<211> LENGTH: 118
<212> TYPE: PRT
<213> ORGANISM: Homo sapiens

<400> SEQUENCE: 6

```
Gln Val Gln Leu Val Gln Ser Gly Gly Gly Val Val Gln Ser Gly Arg
1               5                   10                  15

Ser Leu Arg Leu Ser Cys Ala Ala Ser Gly Phe Lys Phe Ser Gly Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Tyr Tyr Val Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Arg Gln Met Gly Tyr Trp His Phe Asp Leu Trp Gly Arg Gly Thr
            100                 105                 110

Leu Val Thr Val Ser Ser
            115

<210> SEQ ID NO 7
<211> LENGTH: 324
<212> TYPE: DNA
<213> ORGANISM: Homo sapiens

<400> SEQUENCE: 7
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctccgct cactttcggc     300
ggagggacca aggtggagat caaa                                           324

<210> SEQ ID NO 8
<211> LENGTH: 108
<212> TYPE: PRT
<213> ORGANISM: Homo sapiens

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Thr Phe Gly Gly Gly Thr Lys Val Glu Ile Lys
            100                 105

<210> SEQ ID NO 9
<211> LENGTH: 354
<212> TYPE: DNA
<213> ORGANISM: Homo sapiens

<400> SEQUENCE: 9
caggtgcagc tggtggagtc cggggggaggc gtggtccagc ctggggaggtc cctgagactc      60 tcctgtgcag cgtctggatt caccttcaga agctatggca tgcactgggt ccgccaggct     120
ccaggcaagg ggctggagtg ggtggcaatt atatggtatg atggaagtaa aaaaaactat     180
gcagactccg tgaagggccg attcaccatc tccagagaca attccaagaa cacgctgtat     240
ctgcaaatga acagcctgag agccgaggac acggctgtgt attactgtgc gagaggaact     300

```
gggtacaact ggttcgaccc ctggggccag ggaaccctgg tcaccgtctc ctca        354
```

<210> SEQ ID NO 10
<211> LENGTH: 118
<212> TYPE: PRT
<213> ORGANISM: Homo sapiens

<400> SEQUENCE: 10

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Lys Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Tyr Asn Trp Phe Asp Pro Trp Gly Gln Gly Thr
            100                 105                 110

Leu Val Thr Val Ser Ser
        115
```

<210> SEQ ID NO 11
<211> LENGTH: 324
<212> TYPE: DNA
<213> ORGANISM: Homo sapiens

<400> SEQUENCE: 11

```
gaaattgtgt tgacacagtc tccacgcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggac   240
cctgaagatt ttgcagtgta ttactgtcag cagtatggta gctcaccgat caccttcggc   300
caagggacac gactggagat taaa                                          324
```

<210> SEQ ID NO 12
<211> LENGTH: 318
<212> TYPE: DNA
<213> ORGANISM: Homo sapiens

<400> SEQUENCE: 12

```
gacatcctga tgacccagtc tccatcctcc ctgtctgcat ctgtaggaga cagagtcacc    60
atcacttgcc gggcaagtca gggcattagc agtgctttag cctggtatca gcagaaacca   120
gggaaagctc ctaagctcct gatctattat gcatccagtt tgcaaagtgg ggtcccatca   180
aggttcagcg gcagtggatc tgggacggat tacactctca ccatcagcag cctgcagcct   240
gaagattttg caacttatta ctgtcaacag tattatagta cctcactttt cggcggaggg   300
accaaggtgg agatcaaa                                                 318
```

<210> SEQ ID NO 13
<211> LENGTH: 318
<212> TYPE: DNA
<213> ORGANISM: Homo sapiens

<400> SEQUENCE: 13

```
gacatcgtga tgacccagtc tccatcctcc ctgtctgcat ctgtaggaga cagagtcacc    60
atcacttgcc gggcaagtca gggcattagc agtgctttag cctggtatca gcagaaacca   120
gggaaagctc ctaagctcct gatctatgat gcctccagtt tgggaagtgg ggtcccatca   180
aggttcagcg gcagtggatc tgggacagat ttcactctca ccatcagcag cctgcagcct   240
gaagattttg caacttatta ctgtcaacag tattatagta ccctcacttt cggcggaggg   300
accaaggtgg agatcaaa                                                 318
```

<210> SEQ ID NO 14
<211> LENGTH: 318
<212> TYPE: DNA
<213> ORGANISM: Homo sapiens

<400> SEQUENCE: 14

```
gacatccaga tgacccagtc tccattctcc ctgtctgcat ctgtaggaga cagagtcacc    60
atcacttgct gggccagtca gggcattagc agttatttag cctggtatca gcaaaaacca   120
gcaaaagccc ctaagctctt catctattat gcatccagtt tgcaaagtgg ggtcccatca   180
aggttcagcg gcagtggatc tgggacggat tacactctca ccatcagcag cctgcagcct   240
gaagattttg caacttatta ctgtcaacag tattatagta ccctcacttt cggcggaggg   300
accaaggtgg agatcaaa                                                 318
```

<210> SEQ ID NO 15
<211> LENGTH: 318
<212> TYPE: DNA
<213> ORGANISM: Homo sapiens

<400> SEQUENCE: 15

```
gacatcgaga tgacccagtc tccattctcc ctgtctgcat ctgtaggaga cagagtcacc    60
atcacttgct gggccagtca gggcattagc agttatttag cctggtatca gcaaaaacca   120
gcaaaagccc ctaagctctt catctattat gcatccagtt tgcaaagtgg ggtcccatca   180
aggttcagcg gcagtggatc tgggacggat tacactctca ccatcagcag cctgcagcct   240
gaagattttg caacttatta ctgtcaacag tattatagta ccctcacttt cggcggaggg   300
accaaggtgg agatcaaa                                                 318
```

<210> SEQ ID NO 16
<211> LENGTH: 108
<212> TYPE: PRT
<213> ORGANISM: Homo sapiens

<400> SEQUENCE: 16

```
Glu Ile Val Leu Thr Gln Ser Pro Arg Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Asp
65                  70                  75                  80

Pro Glu Asp Phe Ala Val Tyr Tyr Cys Gln Gln Tyr Gly Ser Ser Pro
```

```
                          85                  90                  95

Ile Thr Phe Gly Gln Gly Thr Arg Leu Glu Ile Lys
            100                 105

<210> SEQ ID NO 17
<211> LENGTH: 106
<212> TYPE: PRT
<213> ORGANISM: Homo sapiens

<400> SEQUENCE: 17

Asp Ile Leu Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Leu Thr
                85                  90                  95

Phe Gly Gly Gly Thr Lys Val Glu Ile Lys
            100                 105

<210> SEQ ID NO 18
<211> LENGTH: 106
<212> TYPE: PRT
<213> ORGANISM: Homo sapiens

<400> SEQUENCE: 18

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gly Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Leu Thr
                85                  90                  95

Phe Gly Gly Gly Thr Lys Val Glu Ile Lys
            100                 105

<210> SEQ ID NO 19
<211> LENGTH: 106
<212> TYPE: PRT
<213> ORGANISM: Homo sapiens

<400> SEQUENCE: 19

Asp Ile Gln Met Thr Gln Ser Pro Phe Ser Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Ala Lys Ala Pro Lys Leu Phe Ile
        35                  40                  45
```

Tyr Tyr Ala Ser Ser Leu Gln Ser Gly Val Pro Ser Arg Phe Ser Gly
            50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Tyr Tyr Ser Thr Leu Thr
                85                  90                  95

Phe Gly Gly Gly Thr Lys Val Glu Ile Lys
            100                 105

<210> SEQ ID NO 20
<211> LENGTH: 106
<212> TYPE: PRT
<213> ORGANISM: Homo sapiens

<400> SEQUENCE: 20

Asp Ile Glu Met Thr Gln Ser Pro Phe Ser Leu Ser Ala Ser Val Gly
 1               5                  10                  15

Asp Arg Val Thr Ile Thr Cys Trp Ala Ser Gln Gly Ile Ser Ser Tyr
                20                  25                  30

Leu Ala Trp Tyr Gln Gln Lys Pro Ala Lys Ala Pro Lys Leu Phe Ile
            35                  40                  45

Tyr Tyr Ala Ser Ser Leu Gln Ser Gly Val Pro Ser Arg Phe Ser Gly
            50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Tyr Tyr Ser Thr Leu Thr
                85                  90                  95

Phe Gly Gly Gly Thr Lys Val Glu Ile Lys
            100                 105

<210> SEQ ID NO 21
<211> LENGTH: 354
<212> TYPE: DNA
<213> ORGANISM: Homo sapiens

<400> SEQUENCE: 21
caggtgcagc tggtgcagtc tggggggaggc gtggtccagc ccggagggtc cctgagactc      60
tcctgtgtag cgtctggatt caccttcagt agctatggca tgcactgggt ccgccaggct     120
ccaggcaagg ggctggagtg ggtggcagct atatggtata tggaagaaa acaagactat     180 gcagactccg tgaagggccg attcaccatc tccagagaca attccaagaa cacgctgtat     240
ctgcaaatga acagcctgag agccgaggac acggctgtgt attactgtac gaggggaact     300
gggtacaatt ggttcgaccc ctggggccag ggaaccctgg tcaccgtctc ctca          354

<210> SEQ ID NO 22
<211> LENGTH: 118
<212> TYPE: PRT
<213> ORGANISM: Homo sapiens

<400> SEQUENCE: 22

Gln Val Gln Leu Val Gln Ser Gly Gly Gly Val Val Gln Pro Gly Arg
 1               5                  10                  15

Ser Leu Arg Leu Ser Cys Val Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Ala Ile Trp Tyr Asn Gly Arg Lys Gln Asp Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Gly Thr Gly Tyr Asn Trp Phe Asp Pro Trp Gly Gln Gly Thr
            100                 105                 110

Leu Val Thr Val Ser Ser
            115

<210> SEQ ID NO 23
<211> LENGTH: 321
<212> TYPE: DNA
<213> ORGANISM: Homo sapiens

<400> SEQUENCE: 23
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggccgtggac gttcggccaa     300
gggaccaagg tggaaatcaa a                                               321

<210> SEQ ID NO 24
<211> LENGTH: 321
<212> TYPE: DNA
<213> ORGANISM: Homo sapiens

<400> SEQUENCE: 24
gccatccagt tgacccagtc tccatcctcc ctgtctgcat ctgtatgaga cagagtcacc      60
atcacttgcc gggcaagtca gggcattagc agtgctttag cctggtatca gcagaaacca     120
gggaaagctc ctaagctcct gatctatgat gcctccagtt tggaaagtgg ggtcccatca     180
aggttcagcg gcagtggatc tgggacagat ttcactctca ccatcagcag cctgcagcct     240
gaagattttg caacttatta ctgtcaacag tttaatagtt accctatcac cttcggccaa     300
gggacacgac tggagattaa a                                               321

<210> SEQ ID NO 25
<211> LENGTH: 107
<212> TYPE: PRT
<213> ORGANISM: Homo sapiens

<400> SEQUENCE: 25

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Trp

```
                        85                  90                  95
Thr Phe Gly Gln Gly Thr Lys Val Glu Ile Lys
                100                 105

<210> SEQ ID NO 26
<211> LENGTH: 107
<212> TYPE: PRT
<213> ORGANISM: Homo sapiens

<400> SEQUENCE: 26

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys
                100                 105

<210> SEQ ID NO 27
<211> LENGTH: 5
<212> TYPE: PRT
<213> ORGANISM: Homo sapiens

<400> SEQUENCE: 27

Gly Tyr Gly Met His
1               5

<210> SEQ ID NO 28
<211> LENGTH: 17
<212> TYPE: PRT
<213> ORGANISM: Homo sapiens

<400> SEQUENCE: 28

Val Ile Trp Tyr Asp Gly Ser Lys Lys Tyr Tyr Val Asp Ser Val Lys
1               5                   10                  15

Gly

<210> SEQ ID NO 29
<211> LENGTH: 9
<212> TYPE: PRT
<213> ORGANISM: Homo sapiens

<400> SEQUENCE: 29

Gln Met Gly Tyr Trp His Phe Asp Leu
1               5

<210> SEQ ID NO 30
<211> LENGTH: 11
<212> TYPE: PRT
<213> ORGANISM: Homo sapiens

<400> SEQUENCE: 30

Arg Ala Ser Gln Ser Val Ser Ser Tyr Leu Ala
1               5                   10
```

<210> SEQ ID NO 31
<211> LENGTH: 7
<212> TYPE: PRT
<213> ORGANISM: Homo sapiens

<400> SEQUENCE: 31

Asp Ala Ser Asn Arg Ala Thr
1               5

<210> SEQ ID NO 32
<211> LENGTH: 10
<212> TYPE: PRT
<213> ORGANISM: Homo sapiens

<400> SEQUENCE: 32

Gln Gln Arg Ser Asn Trp Pro Pro Leu Thr
1               5                   10

<210> SEQ ID NO 33
<211> LENGTH: 5
<212> TYPE: PRT
<213> ORGANISM: Homo sapiens

<400> SEQUENCE: 33

Ser Tyr Gly Met His
1               5

<210> SEQ ID NO 34
<211> LENGTH: 17
<212> TYPE: PRT
<213> ORGANISM: Homo sapiens

<400> SEQUENCE: 34

Ile Ile Trp Tyr Asp Gly Ser Lys Lys Asn Tyr Ala Asp Ser Val Lys
1               5                   10                  15
Gly

<210> SEQ ID NO 35
<211> LENGTH: 9
<212> TYPE: PRT
<213> ORGANISM: Homo sapiens

<400> SEQUENCE: 35

Gly Thr Gly Tyr Asn Trp Phe Asp Pro
1               5

<210> SEQ ID NO 36
<211> LENGTH: 12
<212> TYPE: PRT
<213> ORGANISM: Homo sapiens

<400> SEQUENCE: 36

Arg Ala Ser Gln Ser Val Ser Ser Ser Tyr Leu Ala
1               5                   10

<210> SEQ ID NO 37
<211> LENGTH: 7
<212> TYPE: PRT
<213> ORGANISM: Homo sapiens

<400> SEQUENCE: 37

Gly Ala Ser Ser Arg Ala Thr
1               5

<210> SEQ ID NO 38
<211> LENGTH: 9
<212> TYPE: PRT
<213> ORGANISM: Homo sapiens

<400> SEQUENCE: 38

Gln Gln Tyr Gly Ser Ser Pro Ile Thr
1               5

<210> SEQ ID NO 39
<211> LENGTH: 11
<212> TYPE: PRT
<213> ORGANISM: Homo sapiens

<400> SEQUENCE: 39

Arg Ala Ser Gln Gly Ile Ser Ser Ala Leu Ala
1               5                   10

<210> SEQ ID NO 40
<211> LENGTH: 7
<212> TYPE: PRT
<213> ORGANISM: Homo sapiens

<400> SEQUENCE: 40

Tyr Ala Ser Ser Leu Gln Ser
1               5

<210> SEQ ID NO 41
<211> LENGTH: 8
<212> TYPE: PRT
<213> ORGANISM: Homo sapiens

<400> SEQUENCE: 41

Gln Gln Tyr Tyr Ser Thr Leu Thr
1               5

<210> SEQ ID NO 42
<211> LENGTH: 7
<212> TYPE: PRT
<213> ORGANISM: Homo sapiens

<400> SEQUENCE: 42

Asp Ala Ser Ser Leu Gly Ser
1               5

<210> SEQ ID NO 43
<211> LENGTH: 11
<212> TYPE: PRT
<213> ORGANISM: Homo sapiens

<400> SEQUENCE: 43

Trp Ala Ser Gln Gly Ile Ser Ser Tyr Leu Ala
1               5                   10

<210> SEQ ID NO 44
<211> LENGTH: 17
<212> TYPE: PRT
<213> ORGANISM: Homo sapiens

<400> SEQUENCE: 44

Ala Ile Trp Tyr Asn Gly Arg Lys Gln Asp Tyr Ala Asp Ser Val Lys
1               5                   10                  15

Gly

<210> SEQ ID NO 45
<211> LENGTH: 9
<212> TYPE: PRT
<213> ORGANISM: Homo sapiens

<400> SEQUENCE: 45

Gln Gln Arg Ser Asn Trp Pro Trp Thr
1               5

<210> SEQ ID NO 46
<211> LENGTH: 7
<212> TYPE: PRT
<213> ORGANISM: Homo sapiens

<400> SEQUENCE: 46

Asp Ala Ser Ser Leu Glu Ser
1               5

<210> SEQ ID NO 47
<211> LENGTH: 9
<212> TYPE: PRT
<213> ORGANISM: Homo sapiens

<400> SEQUENCE: 47

Gln Gln Phe Asn Ser Tyr Pro Ile Thr
1               5

<210> SEQ ID NO 48
<211> LENGTH: 98
<212> TYPE: PRT
<213> ORGANISM: Homo sapiens

<400> SEQUENCE: 48

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 49
<211> LENGTH: 16
<212> TYPE: PRT
<213> ORGANISM: Homo sapiens

<400> SEQUENCE: 49

Asn Trp Phe Asp Pro Trp Gly Gln Gly Thr Leu Val Thr Val Ser Ser
1               5                   10                  15

<210> SEQ ID NO 50
<211> LENGTH: 17
<212> TYPE: PRT
<213> ORGANISM: Homo sapiens

```
<400> SEQUENCE: 50

Tyr Trp Tyr Phe Asp Leu Trp Gly Arg Gly Thr Leu Val Thr Val Ser
1               5                   10                  15

Ser

<210> SEQ ID NO 51
<211> LENGTH: 12
<212> TYPE: PRT
<213> ORGANISM: Homo sapiens

<400> SEQUENCE: 51

Leu Thr Phe Gly Gly Gly Thr Lys Val Glu Ile Lys
1               5                   10

<210> SEQ ID NO 52
<211> LENGTH: 12
<212> TYPE: PRT
<213> ORGANISM: Homo sapiens

<400> SEQUENCE: 52

Trp Thr Phe Gly Gln Gly Thr Lys Val Glu Ile Lys
1               5                   10

<210> SEQ ID NO 53
<211> LENGTH: 95
<212> TYPE: PRT
<213> ORGANISM: Homo sapiens

<400> SEQUENCE: 53

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro
                85                  90                  95

<210> SEQ ID NO 54
<211> LENGTH: 12
<212> TYPE: PRT
<213> ORGANISM: Homo sapiens

<400> SEQUENCE: 54

Leu Thr Phe Gly Gly Gly Thr Lys Val Glu Ile Lys
1               5                   10

<210> SEQ ID NO 55
<211> LENGTH: 12
<212> TYPE: PRT
<213> ORGANISM: Homo sapiens

<400> SEQUENCE: 55

Ile Thr Phe Gly Gln Gly Thr Arg Leu Glu Ile Lys
1               5                   10

<210> SEQ ID NO 56
```

```
<211> LENGTH: 96
<212> TYPE: PRT
<213> ORGANISM: Homo sapiens

<400> SEQUENCE: 56

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 57
<211> LENGTH: 12
<212> TYPE: PRT
<213> ORGANISM: Homo sapiens

<400> SEQUENCE: 57

Ile Thr Phe Gly Gln Gly Thr Arg Leu Glu Ile Lys
1               5                   10

<210> SEQ ID NO 58
<211> LENGTH: 4
<212> TYPE: PRT
<213> ORGANISM: Homo sapiens

<400> SEQUENCE: 58

Tyr Gly Met His
1

<210> SEQ ID NO 59
<211> LENGTH: 5
<212> TYPE: PRT
<213> ORGANISM: Homo sapiens

<400> SEQUENCE: 59

Asp Ser Val Lys Gly
1               5

<210> SEQ ID NO 60
<211> LENGTH: 16
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 60

Ile Trp Tyr Xaa Gly Xaa Xaa Xaa Xaa Tyr Xaa Asp Ser Val Lys Gly
1               5                   10                  15
```

```
<210> SEQ ID NO 61
<211> LENGTH: 9
<212> TYPE: PRT
<213> ORGANISM: Homo sapiens
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 61

Xaa Xaa Gly Tyr Xaa Xaa Phe Asp Xaa
1               5

<210> SEQ ID NO 62
<211> LENGTH: 9
<212> TYPE: PRT
<213> ORGANISM: Homo sapiens

<400> SEQUENCE: 62

Gly Thr Gly Tyr Asn Trp Phe Asp Pro
1               5

<210> SEQ ID NO 63
<211> LENGTH: 9
<212> TYPE: PRT
<213> ORGANISM: Homo sapiens

<400> SEQUENCE: 63

Gln Met Gly Tyr Trp His Phe Asp Leu
1               5

<210> SEQ ID NO 64
<211> LENGTH: 5
<212> TYPE: PRT
<213> ORGANISM: Homo sapiens

<400> SEQUENCE: 64

Val Thr Val Ser Ser
1               5

<210> SEQ ID NO 65
<211> LENGTH: 8
<212> TYPE: PRT
<213> ORGANISM: Homo sapiens

<400> SEQUENCE: 65

Gly Thr Leu Val Thr Val Ser Ser
1               5

<210> SEQ ID NO 66
<211> LENGTH: 11
<212> TYPE: PRT
<213> ORGANISM: Homo sapiens

<400> SEQUENCE: 66

Trp Gly Arg Gly Thr Leu Val Thr Val Ser Ser
1               5                   10
```

<210> SEQ ID NO 67
<211> LENGTH: 17
<212> TYPE: PRT
<213> ORGANISM: Homo sapiens

<400> SEQUENCE: 67

Glu Met Gly Gly Ile Thr Gln Thr Pro Tyr Lys Val Ser Ile Ser Gly
1               5                   10                  15

Thr

<210> SEQ ID NO 68
<211> LENGTH: 412
<212> TYPE: DNA
<213> ORGANISM: Homo sapiens

<400> SEQUENCE: 68
tgattcatgg agaaatagag agactgagtg tgagtgaaca tgagtgagaa aaactggatt      60
tgtgtggcat tttctgataa cggtgtcctt ctgtttgcag gtgtccagtg tcaggtgcag     120
ctggtggagt ctgggggagg cgtggtccag cctggaggt ccctgagact ctcctgtgca      180
gcgtctggat tcaccttcag tagctatggc atgcactggg tccgccaggc tccaggcaag     240
gggctggagt gggtggcagt tatatggtat gatggaagta ataaatacta tgcagactcc     300
gtgaagggcc gattcaccat ctccagagac aattccaaga acacgctgta tctgcaaatg     360
aacagcctga gagccgagga cacggctgtg tattactgtg cgagagacac ag             412

<210> SEQ ID NO 69
<211> LENGTH: 101
<212> TYPE: PRT
<213> ORGANISM: Homo sapiens

<400> SEQUENCE: 69

Val Gln Cys Gln Val Gln Leu Val Glu Ser Gly Gly Val Val Gln
1               5                   10                  15

Pro Gly Arg Ser Leu Arg Leu Ser Cys Ala Ala Ser Gly Phe Thr Phe
                20                  25                  30

Ser Ser Tyr Gly Met His Trp Val Arg Gln Ala Pro Gly Lys Gly Leu
            35                  40                  45

Glu Trp Val Ala Val Ile Trp Tyr Asp Gly Ser Asn Lys Tyr Tyr Ala
50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Arg
            100

<210> SEQ ID NO 70
<211> LENGTH: 95
<212> TYPE: PRT
<213> ORGANISM: Homo sapiens

<400> SEQUENCE: 70

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile

```
                35              40              45
Tyr Asp Ala Ser Asn Arg Ala Thr Gly Ile Pro Ala Arg Phe Ser Gly
            50              55              60

Ser Gly Ser Gly Thr Asp Phe Thr Leu Thr Ile Ser Ser Leu Glu Pro
65              70              75              80

Glu Asp Phe Ala Val Tyr Tyr Cys Gln Gln Arg Ser Asn Trp Pro
                85              90              95

<210> SEQ ID NO 71

<400> SEQUENCE: 71

000

<210> SEQ ID NO 72
<211> LENGTH: 17
<212> TYPE: PRT
<213> ORGANISM: Homo sapiens

<400> SEQUENCE: 72

Val Ile Trp Tyr Asp Gly Ser Asn Lys Tyr Tyr Ala Asp Ser Val Lys
1               5                   10                  15

Gly

<210> SEQ ID NO 73
<211> LENGTH: 13
<212> TYPE: PRT
<213> ORGANISM: Homo sapiens

<400> SEQUENCE: 73

Trp Val Arg Gln Ala Pro Gly Lys Gly Leu Glu Trp Val
1               5                   10

<210> SEQ ID NO 74
<211> LENGTH: 31
<212> TYPE: PRT
<213> ORGANISM: Homo sapiens

<400> SEQUENCE: 74

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala
                20              25              30
```